US012629216B2

(12) United States Patent
Luciano et al.

(10) Patent No.: US 12,629,216 B2
(45) Date of Patent: May 19, 2026

(54) GRAPHICAL USER INTERFACE FOR A SURGICAL NAVIGATION SYSTEM

(71) Applicant: Augmedics, Inc., Arlington Heights, IL (US)

(72) Inventors: Cristian J. Luciano, San Diego, CA (US); Krzysztof B. Siemionow, Miami, FL (US); Kateryna Parfeniuk, Deerfield, IL (US); Dominik Gaweł, Warsaw (PL); Edwing Isaac Mejía Orozco, Warsaw (PL); Michał Trzmiel, Warsaw (PL)

(73) Assignee: Augmedics, Inc., Arlington Heights, IL (US)

( * ) Notice: Subject to any disclaimer, the term of this patent is extended or adjusted under 35 U.S.C. 154(b) by 27 days.

(21) Appl. No.: 18/557,814

(22) PCT Filed: May 2, 2022

(86) PCT No.: PCT/US2022/027264
§ 371 (c)(1),
(2) Date: Oct. 27, 2023

(87) PCT Pub. No.: WO2022/232685
PCT Pub. Date: Nov. 3, 2022

(65) Prior Publication Data
US 2024/0206988 A1     Jun. 27, 2024

Related U.S. Application Data

(60) Provisional application No. 63/182,753, filed on Apr. 30, 2021.

(51) Int. Cl.
*A61B 34/20* (2016.01)
*A61B 34/00* (2016.01)
(Continued)

(52) U.S. Cl.
CPC .............. *A61B 34/20* (2016.02); *G06T 19/20* (2013.01); *A61B 2034/105* (2016.02);
(Continued)

(58) Field of Classification Search
None
See application file for complete search history.

(56) References Cited

U.S. PATENT DOCUMENTS

2019/0015163 A1     1/2019   Abhari et al.
2019/0053855 A1*    2/2019   Siemionow ............ A61B 90/37
(Continued)

FOREIGN PATENT DOCUMENTS

EP          3445048 A1     2/2019

OTHER PUBLICATIONS

PCT International Search Report and Written Opinion of International Patent Application PCT/US2022/027264, mailed Aug. 12, 2022, 12 pages, International Searching Authority (EPO).

*Primary Examiner* — Daniel F Hajnik
*Assistant Examiner* — Jed-Justin Imperial
(74) *Attorney, Agent, or Firm* — Dinsmore & Shohl LLP

(57) ABSTRACT

A surgical navigation system can include a three-dimensional (3D) display system with a see-through screen; a tracking system configured to track the position and orientation of a surgeon's head, the see-through screen, a patient anatomy and a medical device to provide current position and orientation data; data associated with an operative plan, patient anatomy, and/or the medical device; a surgical navigation image generator configured to generate a surgical navigation image with a three-dimensional image including a first virtual image indicating the planned position and orientation of the medical device according to the operative plan data and a second virtual image indicating a current position and orientation of the medical device.

23 Claims, 26 Drawing Sheets

(51) Int. Cl.

| | |
|---|---|
| *A61B 34/10* | (2016.01) |
| *A61B 90/00* | (2016.01) |
| *G06F 3/01* | (2006.01) |
| *G06T 19/20* | (2011.01) |

(52) U.S. Cl.

CPC ... *A61B 2034/107* (2016.02); *A61B 2034/252* (2016.02); *A61B 2090/365* (2016.02); *A61B 2090/367* (2016.02); *G06F 3/012* (2013.01); *G06T 2210/21* (2013.01); *G06T 2210/41* (2013.01); *G06T 2219/2012* (2013.01); *G06T 2219/2016* (2013.01)

(56) References Cited

U.S. PATENT DOCUMENTS

| | | | | |
|---|---|---|---|---|
| 2020/0375785 A1* | 12/2020 | Hansen | ................. | G16H 30/40 |
| 2021/0196312 A1* | 7/2021 | Plewe | .................. | A61B 34/20 |

* cited by examiner

100

149

103
110
125
123

109

140
106
141
107
105

104 d1 d2

102
122
121
108

101

100

100

125

151

121

124

132

122

140

141

140

144

143

142

145

146

148

147A

147

147B

141

902

963
905

941

1002

1064A

1064B

1041

1102

1163
1164A
1164AI
1164BI
1164B

1202

1263
1264A
1264AI
1264BI
1264B

1302

1363
1364A
1364AI
1364BI
1364B

1402

1463
1464A
1464AI
1464BI
1464B

1502

1463
1464A
1464AI
1464BI
1464B

1502

1563
1564AI
1564AP
1564BI

1502

1563
1564AI
1564AP
1564BI

1602

1663
1664AI
1664AP
1664BI

1602

1663
1664AI
1664AP
1664BC
1664BI

1602

1663
1664AI
1664AP
1664BC
1664BI

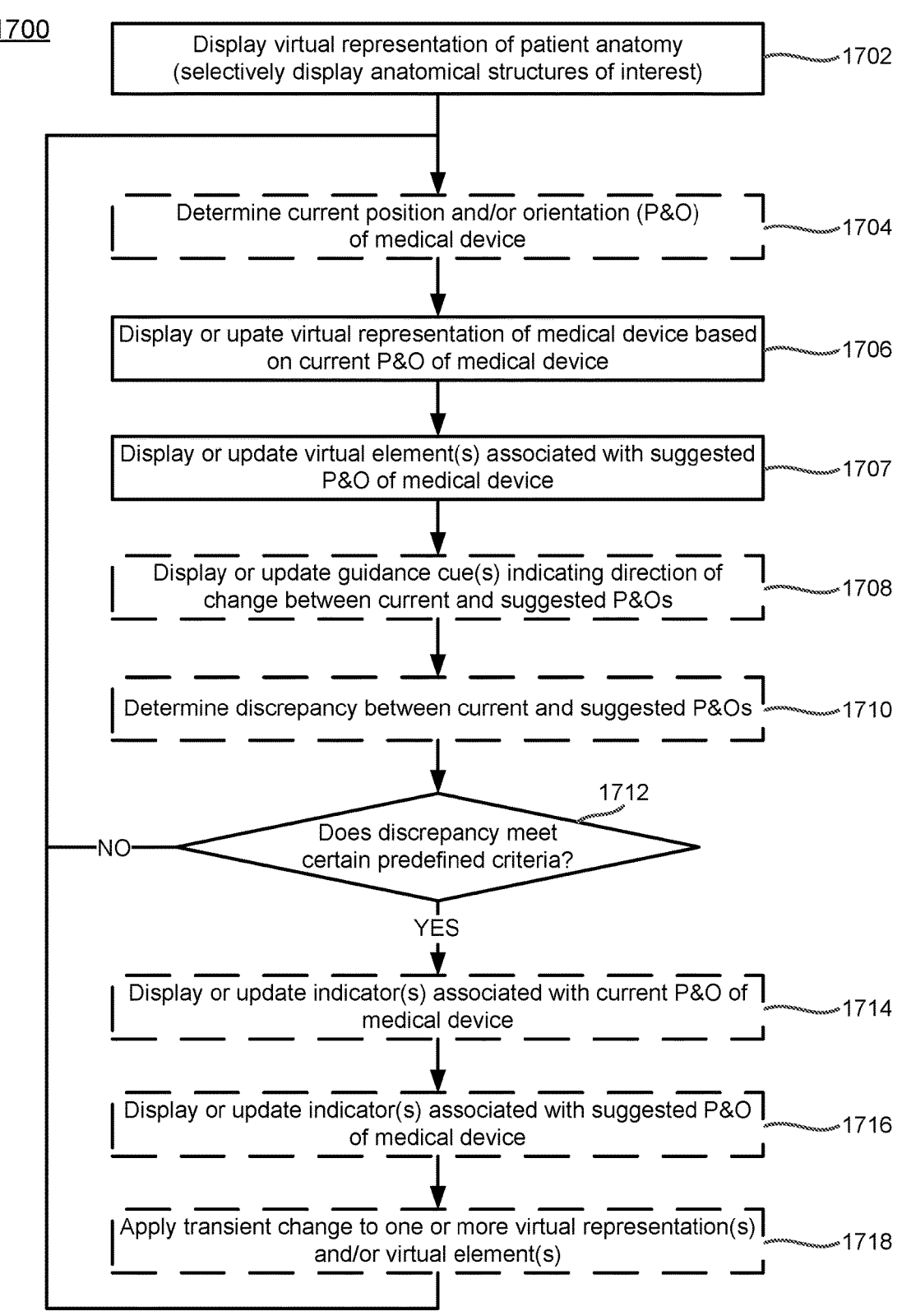

1700

Display virtual representation of patient anatomy (selectively display anatomical structures of interest) ⟶ 1702

Determine current position and/or orientation (P&O) of medical device ⟶ 1704

Display or upate virtual representation of medical device based on current P&O of medical device ⟶ 1706

Display or update virtual element(s) associated with suggested P&O of medical device ⟶ 1707

Display or update guidance cue(s) indicating direction of change between current and suggested P&Os ⟶ 1708

Determine discrepancy between current and suggested P&Os ⟶ 1710

1712

Does discrepancy meet certain predefined criteria?

NO

YES

Display or update indicator(s) associated with current P&O of medical device ⟶ 1714

Display or update indicator(s) associated with suggested P&O of medical device ⟶ 1716

Apply transient change to one or more virtual representation(s) and/or virtual element(s) ⟶ 1718

FIG. 20

GRAPHICAL USER INTERFACE FOR A SURGICAL NAVIGATION SYSTEM

CROSS-REFERENCE TO RELATED APPLICATIONS

This application claims the benefit of U.S. Provisional Application No. 63/182,753, filed Apr. 30, 2021, the content of which is hereby incorporated by reference in its entirety.

TECHNICAL FIELD

The present disclosure relates generally to systems, devices, and methods for providing a graphical user interface for a surgical navigation system, and specifically relates to displaying a virtual representation of patient anatomy.

BACKGROUND

Surgical navigation systems can facilitate visualization of procedures performed by a surgeon on a patient. Some surgical navigation systems can provide pre-operative planning of a surgical procedure as well as image-guided navigation during the surgical procedure. However, surgical navigation systems conventionally include a display monitor placed outside a surgical field such that a surgeon's visual attention has to switch throughout a procedure between the surgical field and the display monitor. This inefficient setup can lead to a disruption of a surgical workflow. Moreover, based on the complexity of the patient anatomy in three-dimensional space, it can be difficult for a surgeon to simultaneously position and orient a surgical instrument in the three-dimensional surgical field based just on the information displayed on the monitor of the navigation system. Similarly, when aligning a surgical instrument with an operative plan, it can be difficult to control the three-dimensional position and orientation of the surgical instrument with respect to the patient anatomy. This can result in an unacceptable degree of error in the preoperative plan that can translate to suboptimal surgical outcomes. Accordingly, additional systems, devices, and methods for displaying a virtual representation of patient anatomy for presurgical planning of surgical instrument trajectory and placement, and intraoperative surgical guidance may be desirable.

SUMMARY

Systems, devices, and methods described herein relate to graphical user interfaces for surgical navigation systems. In some embodiments, systems, devices, and methods described herein relate to displaying a virtual representation of patient anatomy in a field of view of an operating physician (e.g., surgeon).

In some embodiments, a surgical navigation system can include a three-dimensional (3D) display system with a see-through screen; a tracking system configured to track the position and orientation of a surgeon's head, the see-through screen, a patient anatomy and a medical device to provide current position and orientation data; data associated with an operative plan, patient anatomy, and/or the medical device; a surgical navigation image generator configured to generate a surgical navigation image with a three-dimensional image including a first virtual image indicating the planned position and orientation of the medical device according to the operative plan data and a second virtual image indicating a current position and orientation of the medical device.

In some embodiments, an apparatus can include a memory, and a processor operatively coupled to the memory and configured to: determine, based on data associated with an operative plan of a surgical procedure, a planned position and orientation of a medical device in an anatomy of a patient, the medical device configured to be used in a surgical procedure; determine, based on tracking data associated with the medical device, a current position and orientation of the medical device; generate a three-dimensional (3D) image including: a first virtual image indicating the planned position and orientation of the medical device, the first virtual image including a first geometric shape that is shown at the planned position and orientation of the medical device; and a second virtual image indicating the current position and orientation of the medical device, the second virtual image including a second geometric shape that is shown at the current position and orientation of the medical device; modify the 3D image to change a location of the second virtual image to reflect changes in the current position and orientation of the medical device; determine that the current position and orientation of the medical device is near the planned position and orientation of the medical device based on at least one predefined criterion; and in response to determining that the current position and orientation of the medical device is near the planned position and orientation of the medical device, modify at least one characteristic of the first virtual image or the second virtual image.

In some embodiments, an apparatus can include a memory, and a processor operatively coupled to the memory, the processor configured to: determine, based on data associated with an operative plan of a surgical procedure, a planned position and orientation of a medical device in an anatomy of a patient, the medical device configured to be used in a surgical procedure; determine, based on tracking data associated with the medical device, a current position and orientation of the medical device; and generate a three-dimensional (3D) image including: a first virtual image indicating the planned position and orientation of the medical device; and a second virtual image indicating the current position and orientation of the medical device, at least one of the first virtual image or the second virtual image including a geometric shape; and a directional marker located at or near the geometric shape and having a characteristic different than the geometric shape, the directional marker indicating a direction to move the medical device for aligning the current position and orientation of the medical device with the planned position and orientation of the medical device.

BRIEF DESCRIPTION OF THE DRAWINGS

FIG. 20 is a flow chart illustrating a process for displaying a virtual representation of patient anatomy, according to some embodiments.

DETAILED DESCRIPTION

1. Overview of Surgical Navigation Systems

Figure 1:
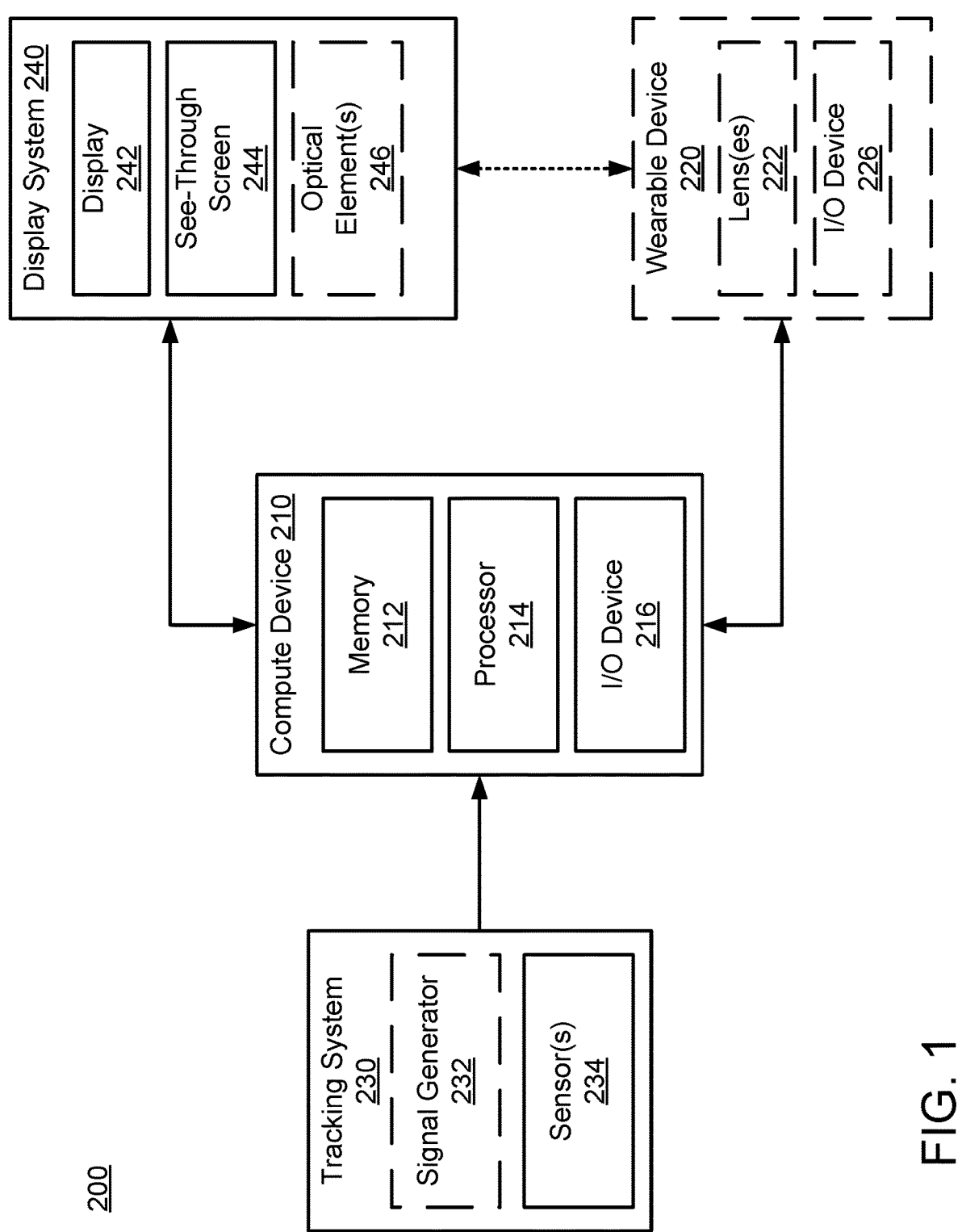
FIG. 1 is a schematic block diagram illustrating a configuration of a surgical navigation system, according to some embodiments.

Systems, devices, and methods described herein relate to surgical navigation systems for displaying a virtual representation of patient anatomy. In some embodiments, the surgical navigation systems described herein may assist a surgeon performing a surgical procedure by providing pre-surgical planning and preoperative diagnostic information. In some embodiments, the preoperative plan and intraoperative data may be displayed in real-time during a procedure. For example, a surgical navigation system may be configured to display a position and orientation of one or more surgical instruments and medical devices (e.g., implants) with respect to presurgical or intraoperative medical imagery datasets corresponding to the patient. These images include pre- and intraoperative images, such as, for example, two-dimensional (2D) fluoroscopic images, X-ray images, ultrasound images, and 3D magnetic resonance imaging (MRI) or computed tomography (CT).

In some embodiments, a surgical navigation system may include a tracking system configured to track objects such as portions of a display of the surgical navigation system, surgical instruments, implantable devices, surgeon anatomy, and/or patient anatomy. For example, a tracking system can include an optical tracking system that has one or more stationary cameras that observes passive reflective markers, active infrared lights, or other objects attached to the instruments, devices, surgeon, and/or the patient. Additionally or alternatively, an optical tracking system can be configured to track one or more physical characteristics or features of an instrument, device, surgeon, and/or the patient. In some embodiments, a tracking system can include an eye-tracker that is configured to measure a gaze and/or eye motion relative to a surgeon's head. In some embodiments, a tracking system can include an electro-magnetic system having a stationary field generator configured to emit an electromagnetic field that can be sensed by coils integrated into tracked medical devices and/or surgical instruments.

As described in more detail herein, in some embodiments, surgical navigation systems enable a surgeon to focus his visual attention on a surgical field by superimposing two- or three-dimensional representations of patient anatomy, surgical guidance, and/or orthogonal image planes virtually onto the area of patient anatomy where the surgery is performed. In this manner, the surgeon can define and execute an operative plan by handling the surgical instruments within a three-dimensional workspace that matches the operative surgical field. Thus, a mental burden of a surgeon may be reduced which may improve surgical and patient outcomes.

In some embodiments, the surgical navigation systems described herein may be used for procedures in traditional operating rooms, interventional radiology suites, mobile operating rooms, outpatient clinics, and/or the like. A procedure may refer to any medical procedure, whether surgical or non-surgical. While certain examples presented herein may generally relate to virtual representations of a spine, it can be appreciated by one of ordinary skill in the art that such systems, devices, and methods can be used to process image data of other portions of patient anatomy, including, for example, vessels, nerves, bone, and other soft and hard tissues near the brain, heart, or other regions of a patient's anatomy. Systems, devices, and methods described herein can be suited for processing several different types of image data, including X-ray, CT, MRI, fluoroscopic, ultrasound, combinations thereof, and the like. In some embodiments, such systems, devices, and methods can process a single image type and/or view, while in other embodiments, such systems, devices, and methods can process multiple image types and/or view. In some embodiments, multiple image types and/or views can be combined to provide richer data regarding a patient's anatomy.

In some embodiments, a surgical navigation system may include a stereoscopic three-dimensional display system with a see-through screen (e.g., a semi-reflective mirror or a wearable device), as well as a tracking system including real-time tracking of a surgeon's head, the see-through screen, a patient anatomy, and a surgical instrument to provide current position and orientation data. In some embodiments, the system may further include a source of an operative plan (e.g., operative plan data), patient anatomy data, and/or a virtual surgical instrument model or data. The system can include a surgical navigation image generator that is configured to generate a surgical navigation image comprising a three-dimensional image that includes a first virtual image indicating a planned or suggested position and orientation of the surgical instrument according to the operative plan data together with a second virtual image of the surgical instrument corresponding to the current or live position and orientation of the surgical instrument, based on the current relative position and orientation of the surgeon's head, the see-through screen, the patient anatomy and the surgical instrument. The system can include a 3D display system that can be configured to show the surgical navigation image on a see-through screen, such that an surgical navigation image is collocated with the patient anatomy in the surgical field underneath the see-through screen when the surgeon is looking from above the see-through mirror toward the surgical field. In other words, the system can include a 3D display system that can present an augmented reality display to the surgeon, whereby the planned or suggested position and orientation of the surgical instrument according to the operative plan data and the current position and orientation of the surgical instrument can be displayed to the surgeon and collocated with the physical patient anatomy and surgical instrument in the surgical field. Suitable examples of augmented reality displays of surgical navigation information are described in U.S. Pat. No. 10,646,285, issued May 12, 2020, U.S. Patent Application Publication No. 2021/0267698, published Sep. 2, 2021, U.S. Patent Application Publication No. 2019/0142519, published May 16, 2019, and U.S. Patent Application Publication No. 2019/0175285, published Jun. 13, 2019, the disclosures of each of which are incorporated herein by reference.

FIG. 1 is a schematic block diagram illustrating a configuration of a surgical navigation system 200 for providing a virtual representation of patient anatomy and/or providing image guidance to physicians, according to some embodiments. For example, the surgical navigation system 200 may facilitate one or more of planning, visualization, and guidance during a surgical procedure. The system 200 can include a compute device 210, an optional wearable device 220, a tracking system 230, and a display system 240. In some embodiments, the compute device 210 can communicate with one or more display systems 240 and/or optional wearable devices 220 to provide digital guidance to one or more surgeons during surgical procedures.

The compute device 210 can be configured to generate virtual representations of patient anatomy, surgical instruments, medical devices, and/or virtual guidance (e.g., to provide image guidance to surgeons during surgical procedures). In some embodiments, the compute device 210 may include a memory 212, a processor 214, and an input/output device 216. While a single compute device 210 is depicted in FIG. 1, it can be appreciated that the compute device 210 may be implemented as a single compute device, or be implemented across multiple compute devices that are connected to each other and/or a network. For example, the compute device 210 may include one or more compute devices such as servers, workstations, desktop computers, laptop computers, portable devices, databases, etc. Different compute device may include component(s) that are remotely situated from other compute devices, located on premises near other compute devices, and/or integrated together with other compute devices.

In some embodiments, the compute device 210 can be located on a server that is remotely situated from one or more of the wearable device 220, tracking system 230, and display system 240. For example, a tracking system 230 and display system 240 can be located in a surgical operating room with a patient, while the compute device 210 can be located at a remote location but be operatively coupled (e.g., via a network) to the tracking system 230 and display system 240. In some embodiments, the compute device 120 can be integrated into one or more of the wearable device 220, tracking system 230, and display system 240. In some embodiments, the compute device 210 can be located within a hospital or medical facility. The compute device 210 can be operatively coupled to one or more databases associated with the hospital (e.g., a hospital database for storing patient information). In some embodiments, the compute device 210 can be available to physicians (e.g., surgeons) for performing evaluation of patient anatomical data and visualization of patient anatomical data, diagnoses, planning, and/or guidance of surgical procedures. In some embodiments, the compute device 210 can be operatively coupled to one or more other compute devices within a hospital (e.g., a physician workstation).

In some embodiments, the compute device 210 can be configured to perform segmentation of patient anatomy. For example, the compute device can be configured to classify portions of images (e.g., each pixel or groupings of pixels) into two different classes, e.g., bone or not bone, types of bones, types of soft tissue, nervous system structures, etc. Suitable examples of convolutional neural network (CNN) models 350 configured for performing segmentation are described in U.S. Patent Publication No. 2019/0105009, published Nov. 11, 2019; U.S. Patent Publication No. 2020/0151507, published May 14, 2020; and U.S. Patent Publication No. 2020/0410687, published Dec. 31, 2020, the contents of each of which are incorporated herein by reference. In some embodiments, the compute device 210 can be configured to perform level identification of patient anatomy. For example, segmented anatomy may be analyzed to perform identification (e.g., level identification of different levels of the spine), geometric measurements and/or evaluations, and/or dimensional measurements and/or evaluations. Example of level identification of spinal anatomy are described in U.S. Patent Application Publication No. 2020/0327721, published Oct. 15, 2020, the contents of which are incorporated herein by reference.

The processor 214 may be any suitable processing device configured to run and/or execute any of the functions described herein. In some embodiments, the processor 214 may be a general purpose processor, a Field Programmable Gate Array (FPGA), an Application Specific Integrated Circuit (ASIC), a Digital Signal Processor (DSP), a Dedicated Graphics Processing Unit (GPU), combinations thereof, and/or the like. In some embodiments, the processor 214 can be configured to perform one or more of image processing, object tracking, virtual imaging, preoperative or operative planning, surgical navigation, and virtual guidance, which can be implemented as one or more programs and/or applications that are tied to hardware components (e.g., processor 214, memory 212, input/output device 216, wearable device 220, tracking system 230, display system 240). In some embodiments, a system bus (not shown) may be configured to enable processor 214, memory 212, input/output device 216, and/or other components of the compute device 210 to communicate with each other and to other devices (e.g., wearable device 220, tracking system 230, display system 240).

Memory 212 may be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, memory 212 can be configured to store instructions that cause processor 214 to execute modules, processes, and/or functions as described herein. Memory 212 can store one or more of anatomical parts data, surgical navigation data, instrument data, medical device data, patient data, procedure data, surgeon data, and/or image data.

The input/output device 216 described herein may include one or more components that are configured to receive inputs and send outputs to other devices (e.g., wearable device 220, tracking system 230, display system 240). In some embodiments, the input/output device 216 can include a graphical user interface, which can include one or more components that are configured to receive input and/or present output to a user. For example, input/output device 216 may include a display device (e.g., a display, a touch screen, etc.), an audio device (e.g., a microphone, a speaker), a keyboard, a mouse, a joystick, a button, a switch, a foot-operable pedal, eye tracker, gaze tracker, and/or other interfaces for receiving information from and/or presenting information to users. In some embodiments, the input/output device 216 can include a communications interface for communicating with other devices, and can include conventional electronics for data communication using a standard communication protocol, e.g., Wi-Fi, Bluetooth®, etc.

In some embodiments, the surgical navigation system 200 may optionally include a wearable device 220 configured to be worn by a surgeon. For example, the wearable device 220 may include an optional set of lenses 222 configured for stereoscopic image visualization. For example, the wearable device 220 may be a set of 3D glasses that facilitate stereoscopic vision. The wearable device 220 may further optionally include an input/output device 226 similar to input/output device 216 described herein. The wearable device 220 may be coupled to the compute device 210 and optionally coupled to the display system 240. In some embodiments, the wearable device 220 may not include any display or lens and/or be in network communication with any other components of the surgical navigation system 200. For example, the wearable device 220 may include an object that is worn by a physician, e.g., for facilitating the tracking of a gaze, movement, location, and/or orientation of the physician's eyes. In an example embodiment, the wearable device 220 can include a set of markers that are worn by a physician, e.g., near the physician's head or eyes. The set of markers can be mounted on a head-worn device (e.g., glasses, goggles, visor, headband, helmet, etc.). The set of markers can then be tracked by a tracking system (e.g., tracking system 230), and such tracking data can be used to determine the gaze, movement, location, and/or orientation of the physician's head or eyes. In some embodiments, the wearable device 220 may include one or more sensors (e.g., optical sensors) for tracking the gaze, movement, location, and/or orientation of the physician's head or eyes, as well as a communication interface that can communicate such information to the compute device 210 or other device operatively coupled to the wearable device 220.

In some embodiments, the surgical navigation system 200 may include a tracking system 230 configured to track patient anatomy, surgical instruments, medical devices, display systems, and/or other objects within a surgical field. In some embodiments, the tracking system 230 may include one or more sensors 234 and an optional signal generator 232. The signal generator 232 may be configured to generate one or more signals (e.g., electro- and/or magnetic signals) that can be used to track the location of one or more objects. For example, the signal generator 232 can be configured to generate electromagnetic systems that can be received at one or more sensor(s) 234 or receivers (e.g., positioned in a medical device or instrument), and such sensors can be configured to transmit their location and/or orientation to a compute device (e.g., compute device 210). In some embodiments, the tracking system 230 can include one or more sensor(s) 234 that can be configured to track physical objects or features of one or more of the patient anatomy, surgical instruments, medical devices, display systems, and/or other objects within a surgical field. For example, the tracking system 230 can include optical sensors configured to track physical markers that are located at one or more of the patient anatomy, surgical instruments, medical devices, display systems, etc. Alternatively, the tracking system 230 can include cameras that are configured to capture image data of a surgical field, and such image data can be processed to track one or more physical features or characteristics of an object. In still other embodiments, other suitable forms of object tracking can be used with systems, devices, and methods described herein.

In some embodiments, the surgical navigation system 200 may include a display system 240 configured to display a virtual representation of one or more of patient anatomy, surgical instrument, medical device, and surgical guidance. For example, the display system 240 may include a display 242, a transmissive (e.g., see-through) screen 244, and an optional optical element 246. The display 242 can include a processor configured to generate a graphical user interface including a surgical navigation image as described herein. The display 242 can be configured to receive image data, tracking data, and/or other data from other components of surgical navigation system 200 (and/or other devices operatively coupled to surgical navigation system 200, as described with reference to FIG. 2). The display 242 can then generate a surgical navigation image for presenting on a see-through screen 244. The display can include light-emitting diodes (LEDs), lasers, or other light sources configured to emit or produce the surgical navigation image. The see-through screen 244 can be configured to be partially transmissive and partially reflective. For example, the see-through screen 244 can be configured to be about 50% transmissive and about 50% reflective. Alternatively, the see-through screen 244 can be configured to be more or less transmissive, e.g., between about 30% to about 70% transmissive, including all sub-ranges and values therebetween. The optical element(s) 246 can include one or more of a lens, a projector, a mirror or reflective surface, etc. Such optical element(s) 246 are optional, and when present, can be configured to scale, transform, project, and/or otherwise manipulate a surgical navigation image generated by the display 242 for viewing by a surgeon at the see-through screen 244.

In some embodiments, the display system 240 can be configured to present a three-dimensional display (e.g., via wearable device 220 and/or a 3D projector or screen). In some embodiments, the surgical navigation system 200 can be configured to display a position and/or orientation of one or more surgical instrument(s) and implant(s) with respect to presurgical or intraoperative medical image data of the patient anatomy. The image data can be provided, for example, by an imaging device 370 (as discussed in more detail with respect to FIG. 2), and the surgical navigation system 200 can use the image data to generate a virtual representation of one or more anatomical parts of interest along with position and/or orientation data associated with a surgical device. Suitable examples of surgical navigation systems are described in U.S. Patent Application Publication No. 2019/0053851, published Feb. 21, 2019, and incorporated herein by reference.

In some embodiments, the surgical navigation system 200 can receive tracking data from tracking system 230, e.g., of a portion of the distal system 240, the patient anatomy, the surgeon anatomy (e.g., a surgeon's head), a surgical device, an implantable device, etc. as well as patient anatomy data, surgical device data, etc. that was obtained preoperatively, and use this information to generate a surgical navigation image. As described above, the surgical navigation image can include virtual representations of portion(s) of a surgical device, an implantable device, the patient anatomy, etc. In some embodiments, the surgical navigation image can include a virtual representation of a medical device (e.g., surgical tool or implant) in a planned location and/or orientation, e.g., based on preoperative planning data. In some embodiments, the surgical navigation image can include a virtual representation of patient anatomy of interest as well as neighboring anatomy. In some embodiments, the surgical navigation image can include a virtual representation of at least a portion of a medical device in its current position and/or orientation, e.g., based on tracking data associated with the medical device during a surgery. Further details of a surgical navigation image are provided with reference to FIG. 8 below.

Figure 2:
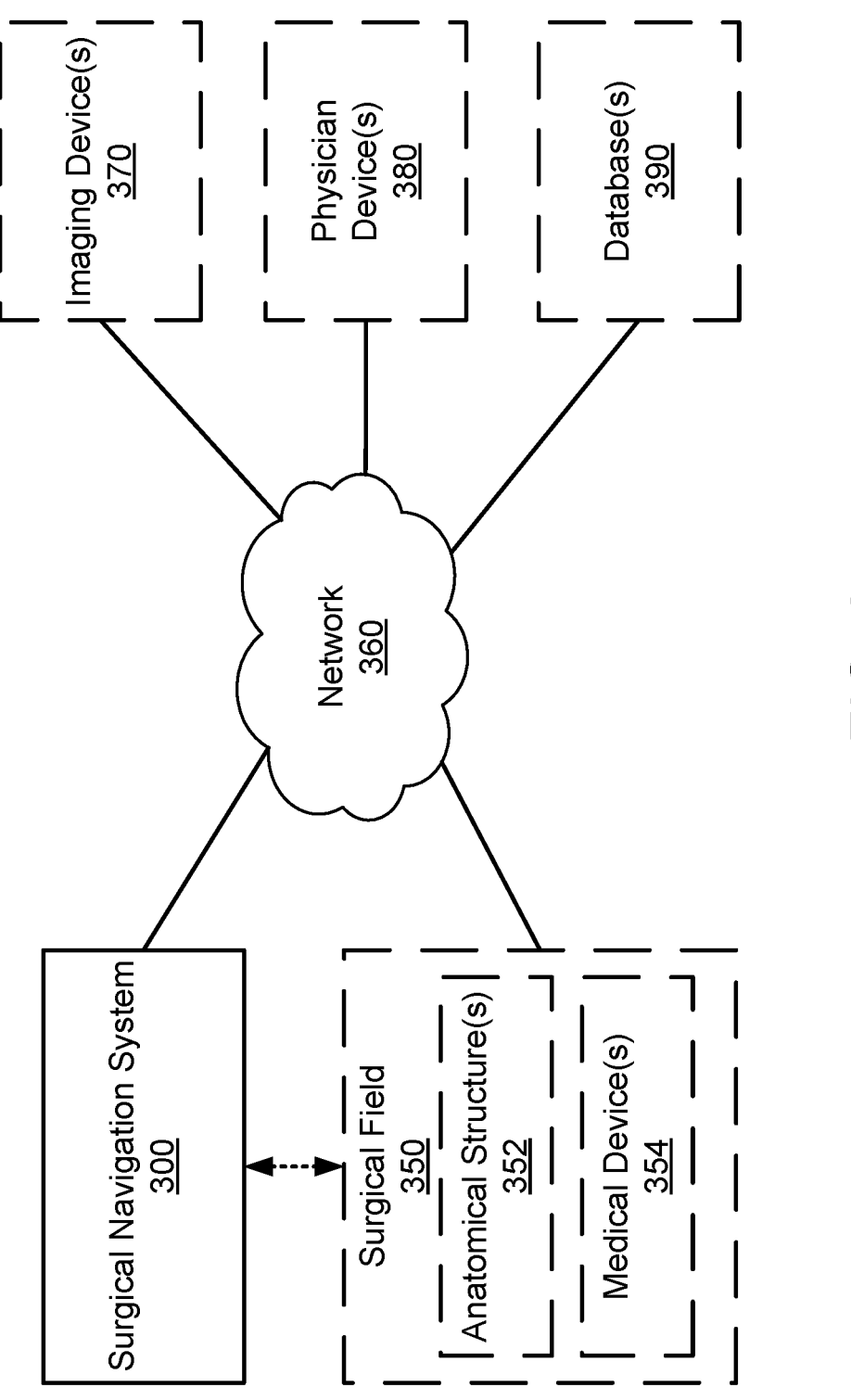
FIG. 2 is a schematic block diagram illustrating a configuration of a surgical navigation system, according to some embodiments.

FIG. 2 is a schematic block diagram illustrating a configuration of a surgical navigation system 300 for surgical planning and/or navigation, according to some embodiments. Surgical navigation system 300 can be structurally and/or functionally similar to surgical navigation system 200 and/or other surgical navigation systems described herein, and therefore include components that are structurally and/or functionally similar to those of surgical navigation system 200 and/or other surgical navigation systems described herein.

The surgical navigation system 300 may operate or be used by a surgeon operating in a surgical field 350. The surgical field 350 may include one or more anatomical structures 352 and medical devices 354 (e.g., surgical tool, implant, or other medical device). Surgical navigation system 300 may be coupled to one or more networks 360 which may be further optionally coupled to one or more imaging devices 370, physician devices 380, and databases 390. Network 360 may be any type of network (e.g., a local area network (LAN), a wide area network (WAN), a virtual network, a telecommunications network) implemented as a wired network and/or wireless network and used to operatively couple compute devices, including system 300. As shown in FIG. 2, a connection may be defined between the surgical navigation system 300 and any one of imaging device(s) 370, physician device(s) 380, and/or other compute device(s) (e.g., databases 390, servers, etc.). In some embodiments, the surgical navigation system 300 may communicate with imaging device(s) 370, physician device(s) 380, and/or database(s) 390 (e.g., send data to and/or receive data from such devices) and with the network 360 via intermediate networks and/or alternate networks (not shown in FIG. 2). Such intermediate networks and/or alternate networks may be of a same type and/or a different type of network as network 360. Each of the surgical navigation system 300, imaging device(s) 370, physician device(s) 380, and database(s) 390 may be any type of device configured to send data over the network 360 to send and/or receive data from one or more of the other devices.

The imaging device 370 may refer to any device configured to image anatomical structures of a patient (e.g., anatomical structure(s) 352). In some embodiments, the imaging device 370 may include one or more sensors for measuring signals produced by various imaging technologies. The imaging device 370 can employ a non-invasive technology to image a patient's anatomy. Non-limiting examples of imaging devices include CT scanners, MRI scanners, X-ray devices, ultrasound devices, combinations thereof, and the like. The image data generated by the imaging device 370 may be transmitted to any of the devices connected to network 360, including, for example, surgical navigation system 300. In some embodiments, the image data generated by the imaging device 160 can include a 2D image of an anatomical structure. In some embodiments, the image data generated by the imaging device 370 can include a plurality of 2D image scans that together provide image data for a 3D volume. The imaging device 370 can provide the image data to a surgical navigation system 300 such that the surgical navigation system can generate one or more virtual representations of the patient anatomy (e.g., for use in image-guided surgery). Optionally, the imaging device 370 can transmit the image data to the surgical navigation system 300 or another compute device, which can be configured to perform segmentation and/or level identification of the patient anatomy and/or label different anatomical parts of interest in the patient anatomy.

The physician device(s) 380 can be compute devices that are used by a physician (e.g., surgeon) to perform preoperative or operative planning. For example, the physician device 380 can be a workstation (e.g., compute device) that is used by the physician to evaluate a patient's condition (e.g., spinal deformity) and perform preoperative planning (e.g., selection of implant(s) for addressing deformity, surgical plan for placing the implant(s), etc.). The databases(s) 390 can be configured to store information regarding patient anatomy (e.g., anatomical structure(s) 352), medical devices (e.g., medical device(s) 354), imaging device(s) 370, and/or physician device(s) 380. In some embodiments, the database(s) 390 can be configured to store preoperative image data of the anatomical structure(s) 352, and such data can be provided to the surgical navigation system 300 or other compute devices during a surgical procedure (e.g., for facilitating segmentation, identification, and/or display of the anatomical structure(s) 352). In some embodiments, the database(s) 390 can be configured to store object data of one or more medical devices (e.g., surgical tools or implants), and can be configured to supply that data to surgical navigation system 300 or other compute devices during a surgical procedure (e.g., for facilitating object tracking, generating preoperative or operative plan data, etc.).

Figure 3A:
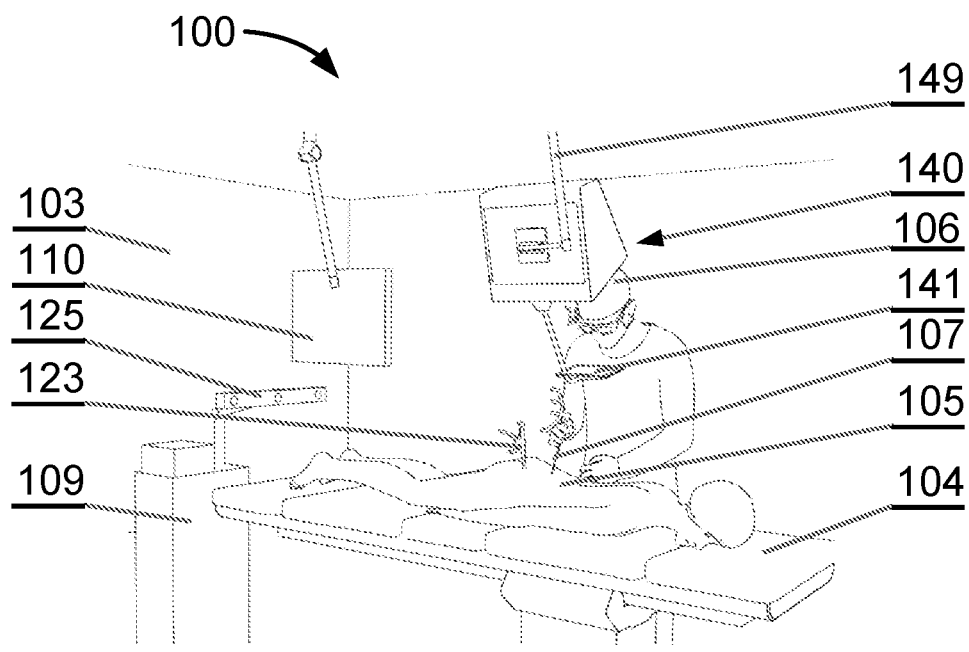
FIG. 3A is a perspective view illustrating an operating room including a patient and surgeon operating a surgical navigation system, according to some embodiments.
Figures 3B, 3C:
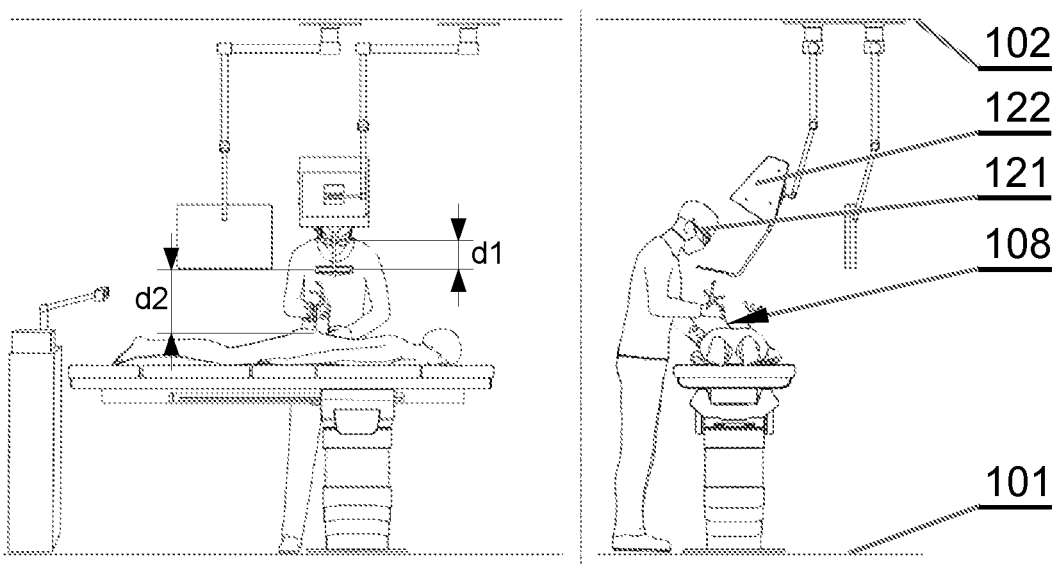
FIG. 3B is a side view illustrating the operating room shown in FIG. 3A, according to some embodiments.
FIG. 3C is a rear view illustrating the operating room shown in FIG. 3A, according to some embodiments.

FIG. 3A is a perspective view illustrating an operating room including a patient 105 and a surgeon 106 utilizing a surgical navigation system 100. The surgical navigation system 100 can be structurally and/or functionally similar to other surgical navigation systems described herein, including, for example surgical navigation systems 200, 300. As such, the surgical navigation system 100 can include components that are structurally and/or functionally similar to those of such surgical navigation systems. The patient 105 may be disposed on a patient platform 104 coupled to a floor 101 as shown in FIG. 3C. One or more surgical instruments 107 and a patient anatomy marker array 123 may be disposed within a surgical field 108. The surgical navigation system 100 may include a display system 140 coupled to one or more of a floor 101, ceiling 102, sidewall 103, and patient platform 104 via adjustable holder 149 (e.g., surgical boom). The holder 149 may be configured to adjust a position (e.g., height) and/or orientation of the display system 140 with respect to the surgeon 106 and patient 105 to accommodate the surgeon and any requirements of the procedure.

The display system 140 may include a display position marker array 122 and transmissive screen 141 (e.g., see-through mirror or half-silvered mirror, such as, for example, see-through screen 244) configured for viewing by the surgeon 106. The surgeon 106 can see the real world behind the screen 141 (e.g., physical objects such as the patient anatomy and/or medical devices in the real environment) but the screen 141 also reflects the surgical navigation image generated by a compute device of the display system 140 located above it (e.g., a display 242 or processor included in the display 242). In some embodiments, the transmissive screen 141 can have a reflective and transmissive rate of about 50% reflective and 50% transmissive. While not depicted, it can be appreciated that the display system 140 can include a processor or be operatively coupled to a processor that is configured to generate surgical navigation images, including virtual representations of medical devices, patient anatomy, etc.

The head of the surgeon 106 may be coupled to a head position marker array 121. The head position marker array 121 can be coupled to glasses, a headband, or other wearable device worn by the surgeon. A fiducial marker tracker 125 (e.g., including one or more sensor(s) of a tracking system, such as, for example, tracking system 230) may be configured to track a position and/or orientation of each of the marker arrays 121-123, e.g., to track the head of the surgeon, the display system, and the patient anatomy, respectively.

In some embodiments, the display system 140 may be configured to output a surgical navigation image towards the screen 141 that is partially transmissive and partially reflective such that the surgical navigation image can be collocated with the patient anatomy in the surgical field 108 underneath the screen 141 when viewed by the surgeon 106 looking from above the screen 141 toward the surgical field 108. As such, the display system 140 can be configured to provide an augmented reality view of the environment to the surgeon. In particular, the display system 140 can be configured to provide information regarding medical devices (e.g., surgical tools, implants), patient anatomy, and/or pre- or intra-operative plans (e.g., surgical guidance) to the surgeon in an augmented reality setting. In some embodiments, the display system 140 may be positioned inside of, outside of, or near a surgical field including the patient anatomy being operated on. For example, the display system 140 can form part of a compute device (e.g., laptop, personal computer, workstation) that is disposed outside of a surgical field but within view of a surgeon or operator. The surgeon can then view the patient anatomy and/or surgical guidance displayed on the display system 140 when operating on the patient. Alternatively, the display system 140 can be configured to display on a surface near the patient anatomy a virtual representation of the patient anatomy and/or surgical guidance, where the virtual elements are display near but not collocated with the physical or actual patient anatomy and instruments.

Figure 4A:
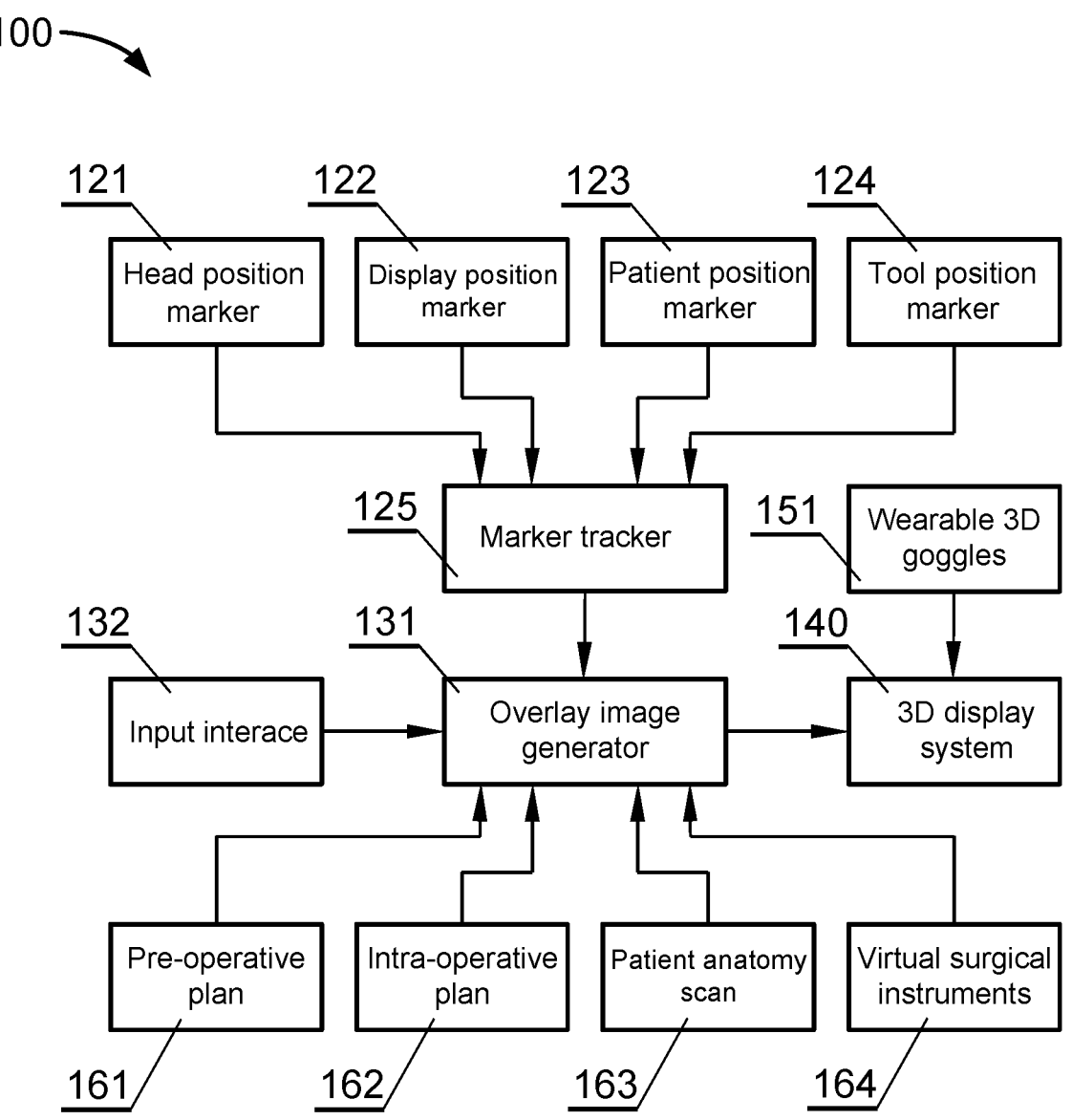
FIG. 4A is a schematic block diagram illustrating a tracking system and display system of a surgical navigation system, according to some embodiments.

In some embodiments, the surgical navigation system 100 can include one or more compute devices, such as, for example, a compute device configured to generate surgical navigation images (e.g., overlay image generator 131 as depicted in FIG. 4A), a compute device configured to determine a location and/or orientation of one or more objects (e.g., a processor of a tracking system, such as, for example, fiducial marker tracker 125). In some embodiments, one or more components of the surgical navigation system 100 may be disposed in separate housings. For example, a surgical image generator 131 can be implemented in a dedicated compute device 109, such as a stand-alone computer, which may have its own input controllers (e.g., I/O devices) and display(s).

FIG. 3B is a side view illustrating the operating room shown in FIG. 3A. FIG. 3C is a rear view illustrating the operating room shown in FIG. 3A. In some embodiments, a distance d1 between the surgeon's eyes and the transmissive screen 141 may be shorter than a distance d2 between the transmissive screen 141 and the operative field at the patient anatomy 105 being operated. The distance d1 may be less than the distance d2 such that additional space is provided to the surgeon between the screen 141 and the patient anatomy. This can facilitate, for example, greater ability to navigate and/or manipulate instruments by the surgeon.

FIG. 4A is a schematic block diagram illustrating components of the tracking system and the display system of the surgical navigation system 100, according to embodiments. The tracking system can be functionally and/or structurally similar to the tracking system 230 described with reference to FIG. 1, as well as other tracking systems described herein. For example, the tracking system may be configured for real-time tracking of the position and/or orientation of a set of objects. The tracking system may comprise a set of arranged fiducial markers 121-124 monitored by a fiducial marker tracker 125. The set of fiducial markers 121-124 can include one or more 4-point marker arrays that are attached to each of the surgeon's head, the display, the patient anatomy, and a surgical tool, respectively. The set of fiducial markers 121-124 can be tracked by a three-camera sensor of the fiducial marker tracker 125, e.g., to provide movement along six degrees of freedom. For example, a head position marker array 121 can be configured to be attached to a surgeon's head for tracking of the position and/or orientation of the surgeon and/or the direction of gaze of the surgeon. In some embodiments, the head position marker array 121 can be integrated with a wearable device 151 (e.g., similar to wearable device 220). Additionally or alternatively, the head position marker array 121 can be attached to a strip worn on the surgeon's head. A display position marker array 122 can be configured to attach to the screen 141 of the display system 140 for tracking a position and/or orientation of the screen 141. The position and/or orientation of the screen 141 may be adjusted to meet the needs of the surgeon. A patient anatomy marker array 123 (e.g., patient position marker) can be configured to attach to a set of predetermined portions of the patient for tracking a position and/or orientation of the patient anatomy. A surgical instrument marker array 124 (e.g., tool position marker) can be configured to attach to one or more surgical instruments and/or medical devices for tracking a position and/or orientation of the surgical instruments. In some embodiments, one or more of fiducials of the marker arrays may be non-coplanar to improve the accuracy of the tracking system. In some embodiments, the fiducial marker tracker 125 may be configured to determine a position and/or orientation of one or more of the head position marker array 121, display position marker array 122, patient anatomy marker array 123, and surgical instrument marker array 124. Specifically, the sensors of the fiducial market tracker 125 can collect data regarding the set of marker arrays and send that information to an onboard or remote processor, which can be configured to process the sensor data and determine the position and orientation of the arrays and their respective objects.

The surgical navigation system 100 can include a surgical navigation image generator or overlay image generator 131 (e.g., similar to compute device 210) configured to generate a surgical navigation image to be viewed via the screen 141 of the display system. In some embodiments, the surgical navigation image generator 131 may be configured to generate a surgical navigation image such as that shown in FIGS. 6B and 8-19B. The surgical navigation image generator 131 can be configured to receive information, including, for example, pre-operative plan 161 data, intra-operative plan 162 data, patient anatomy scan 163 data, and/or virtual surgical instruments 164 data. The image generator 131, based on such information as well as tracking data received from fiducial marker tracker 125, can generate surgical navigation images that can provide surgical guidance to the surgeon. Such surgical guidance can include, for example, information regarding the patient anatomy (e.g., segmentation data of anatomical parts of interest and/or neighboring parts), information regarding pre- or intra-operative plans (e.g., visual guides that indicate proper positioning and/or orientation of a medical device), and/or information regarding the real location of objects in the surgical field (e.g., medical devices, surgical devices, robotic devices, etc.). In some embodiments, the surgical navigation system 100 may include an input interface 132, e.g., for receiving inputs from a user that can be used to control the operation of the image generator 131. The input interface 132 may be similar to input/output device 216 as described above.

As described herein, the surgical navigation system 100 can be configured to generate, via the see-through screen 141, an augmented reality image such as that shown in FIGS. 6B and 8-19B, where hidden or obscured portions of a surgical instrument or other medical device and/or patient anatomy can be shown to a surgeon. For example, when a surgeon is operating on a patient, certain portions of the patient anatomy (e.g., spine, nerves, etc.) that lie under the patient's skin or other tissue may not be readily visible to the surgeon. Portions of a surgical instrument or other medical device that are inserted within the patient anatomy, e.g., via incisions or other openings, may also not be visible to a surgeon. As such, surgical navigation systems as described herein can be configured to provide virtual representations or virtual images that correspond to the hidden portions of the patient anatomy and/or medical devices. In some embodiments, these virtual representations can be overlaid on top of the physical or real devices or anatomy. In some embodiments, the virtual representation or virtual image corresponding to a medical device can be shown to extend from the visible portion of the medical device in the real environment, e.g., using the system 100 and other surgical navigation systems as described herein.

Figure 4B:
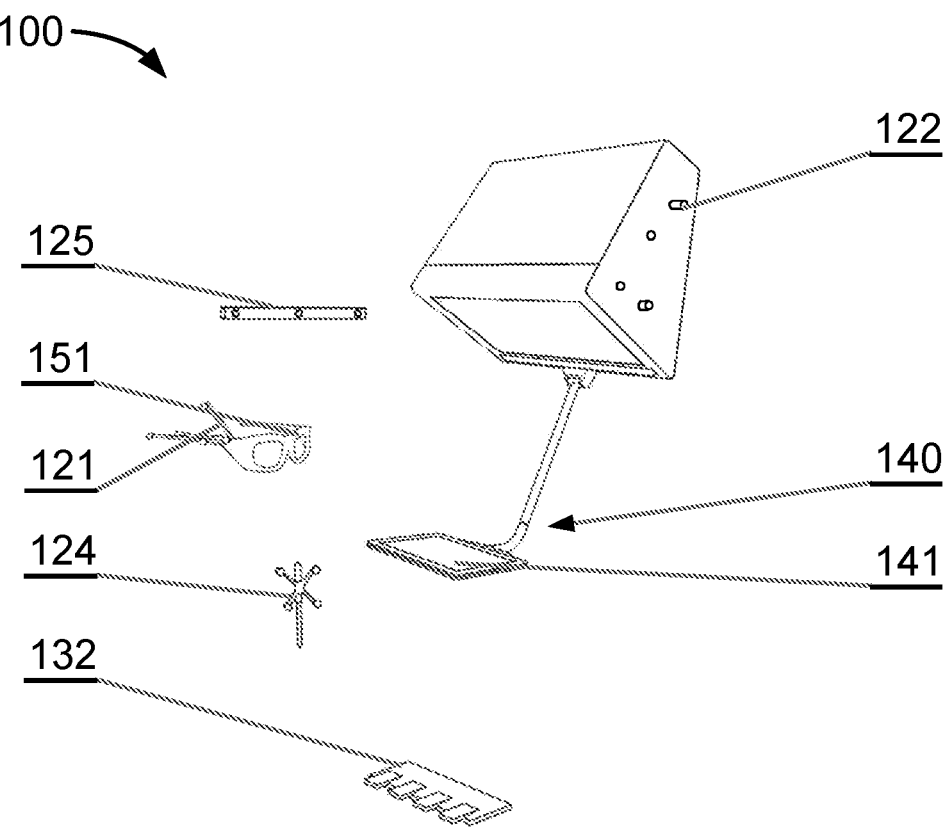
FIG. 4B is a perspective view illustrating a tracking system and display system of a surgical navigation system, according to some embodiments.

FIG. 4B is an isolated view of certain components of the tracking system and the display system of the surgical navigation system 100. As described above, the display system 140 can include the see-through screen 141. In some embodiments, the display system 140 can be coupled to an input interface or I/O device 132, such as, for example, a foot pedal. The input interface 132 can be configured to receive inputs from a user, which can be used to control the operation of the display system 140 and/or other components of the surgical navigation system 100. The tracking system can include a fiducial marker tracker 125 that can be configured to track one or more marker arrays, including a marker array 121 on a wearable device 151 (e.g., stereoscopic three-dimensional glasses), a surgical instrument marker array 124, and a marker array 122 on the display system 140.

Figure 5A:
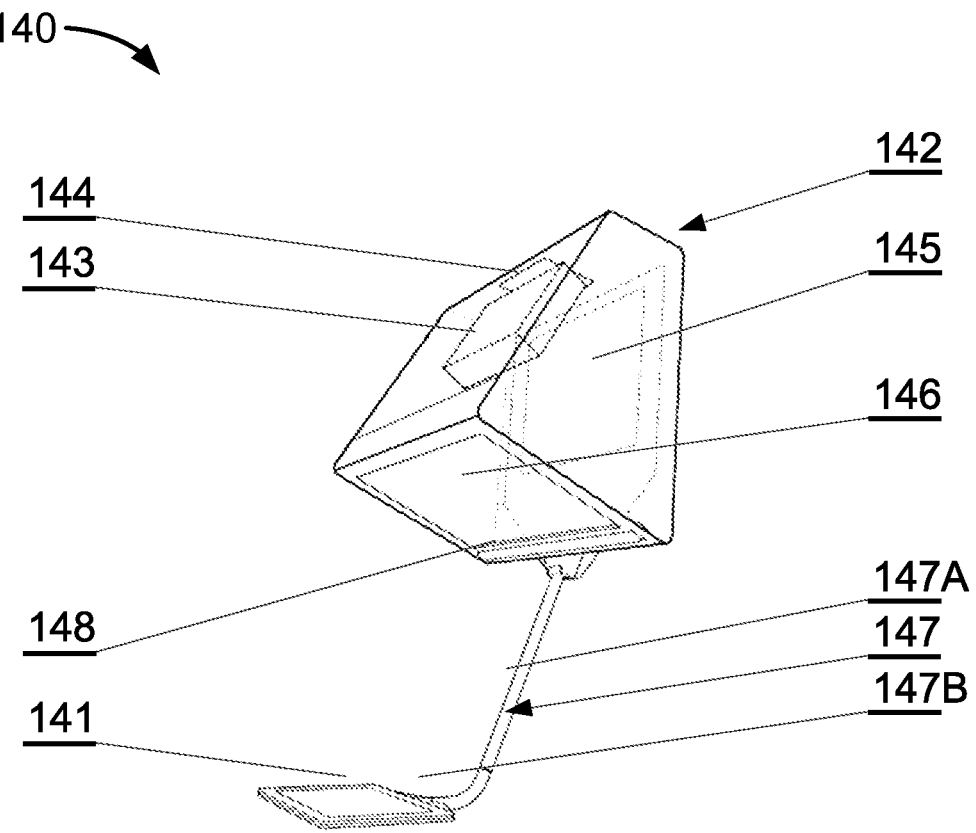
FIG. 5A is a perspective view illustrating a display system of a surgical navigation system, according to some embodiments.

In some embodiments, the display system 140 can be configured to provide a relatively large and bright image for viewing without a wide-angle lens. For example, FIG. 5A is a perspective view illustrating the display system 140 including a stereoscopic three-dimensional display 142 having a stereoscopic three-dimensional projector 143 (e.g., a digital light processing (DLP) projector) configured to generate and output an image sequentially to a first opaque mirror 144, a second opaque mirror 145, a projection screen 146 (e.g., glass panel, stereoscopic three-dimensional display), and the screen 141 (e.g., augmented reality visor). The projection screen 146 may be a rear-projection screen, and the image output by the projection screen 146 may be partially reflected by the screen 141. The projection screen 146 can be configured to enlarge the image generated by the stereoscopic three-dimensional projector 143 such that image reflected at the screen 141 is easily visible and bright to the surgeon. The projection screen 146 may be coupled to the screen 141 via an arm 147. The display system 140 may further include an eye tracker 148 configured to monitor the position and/or orientation of the eyes of the surgeon. The eye tracker 148 can be angled to capture position, movement, or other data of the surgeon's eyes, e.g., using optical or other mechanisms. The gaze data generated by eye tracker 148 may be provided to the surgical navigation image generator 131, e.g., for generating surgical navigation images that align with the surgeon's view. As depicted, the eye tracker 148 is located on the display 142. Additionally or alternatively, the eye tracker 148 (or additional eye trackers) can be located on the see-through screen 141 and/or wearable device 151.

In some embodiments, the arm 147 may include a first portion 147A coupled to a housing of display 142 and a second portion 147B releasably coupled to the first portion 147A. In some embodiments, a protective sleeve may be disposed over the first portion 147A. In some embodiments, the screen 141 and second portion 147B may be configured as single-use components (e.g., disposable) while the first portion 147A and display 142 may be durable or reusable components. In some embodiments, the length, angle, and/or other configuration of the arm 147 can be adjusted, e.g., to adjust a position and/or orientation of the screen 141. In such embodiments, the position and/or orientation of the screen 141 can be tracked, e.g., via the tracking system. For example, the arm 147 may be folded toward the display 142 to increase an open space below the display 142.

Figure 5B:
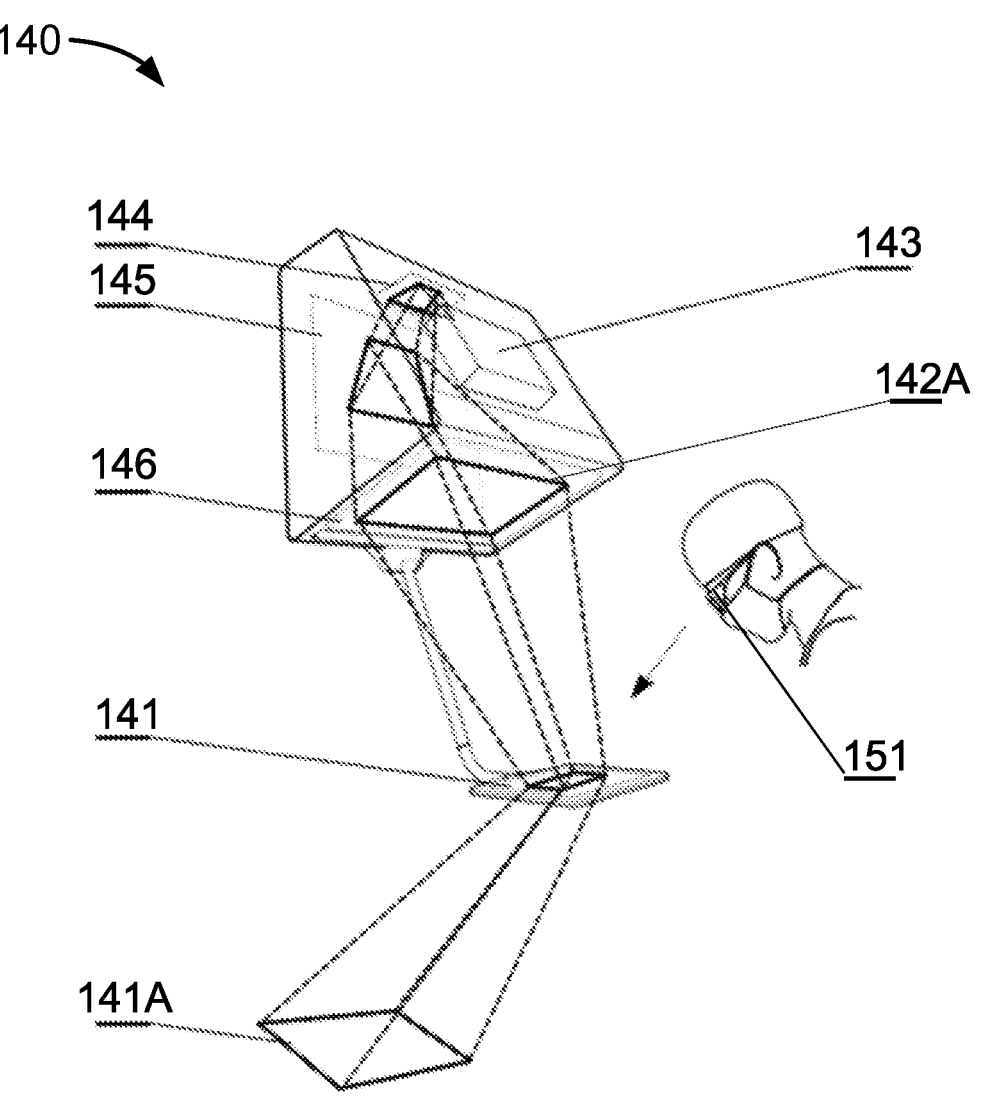
FIG. 5B is a perspective view illustrating a surgeon using the display system shown in FIG. 5A, according to some embodiments.

FIG. 5B is a perspective view illustrating a surgeon using the display system 140, according to embodiments. The dashed lines in FIG. 5B depict the path of the image projections and corresponding solid lines depict the image generated on a corresponding surface (e.g., projection screen 146, see-through screen 141, patient anatomy). The projector 143 can be configured to generate a surgical navigation image that is reflected by opaque mirrors, 144, 145 onto the projection screen 146. The image 142A at the projection screen 146 is then projected toward the see-through screen 141. Surgical navigation image 141A (e.g., augmented reality image) can be output onto patient anatomy from the see-through screen 141. Stated differently, surgical navigation image 141A can be visible to the surgeon on the see-through screen 141 such that virtual representations of objects within the surgical navigation image 141A are collocated with their corresponding physical objects in the real environment as viewed by the surgeon.

Figure 6A:
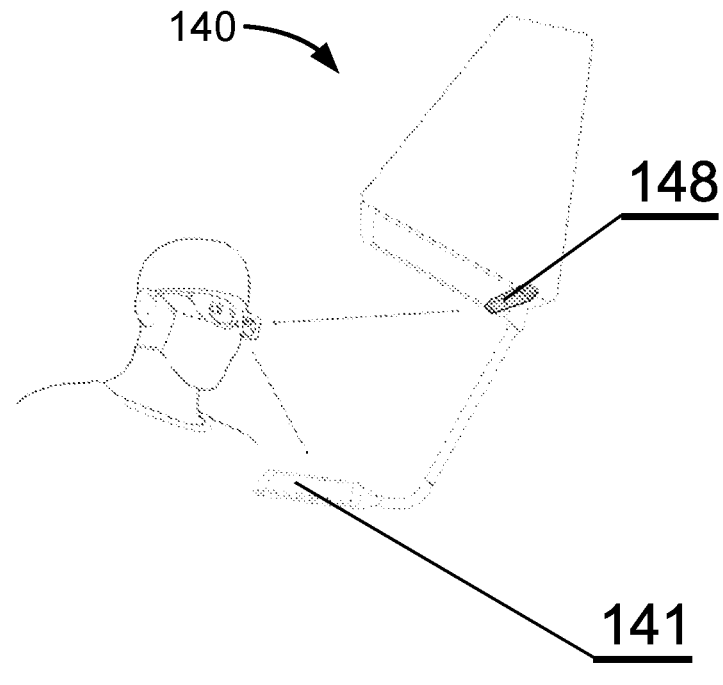
FIG. 6A is a perspective view illustrating eye tracking using a surgical navigation system, according to some embodiments.
Figure 6B:
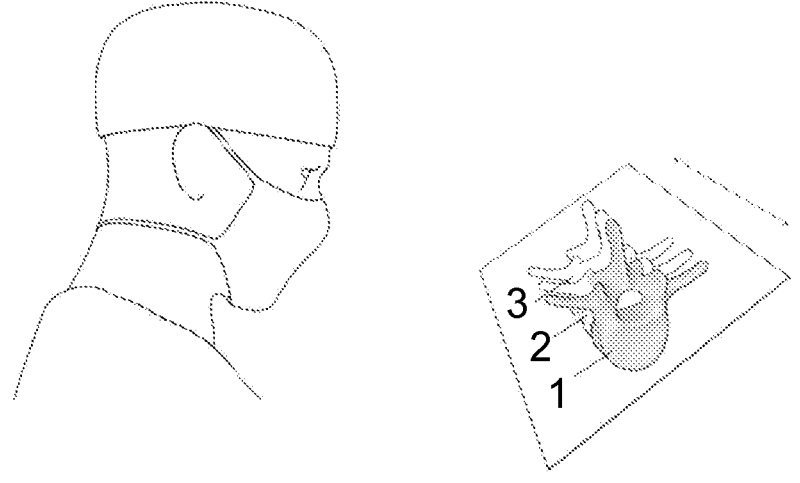
FIG. 6B is perspective view of a surgical navigation image based on the eye tracking shown in FIG. 6A, according to some embodiments.

FIG. 6A is a perspective view illustrating eye tracking using the surgical navigation system 100. As described above, the display system 140 may include an eye tracker 148 configured to determine a surgeon's gaze relative to a partially transmissive and partially reflective and partially transmissive screen 141. For example, the eye tracker 148 may be configured to emit infrared light to illuminate the eyes of the surgeon without affecting the surgeon's vision. The reflection and refraction of the infrared light on the eyes may be measured by the eye tracker 148 to determine a gaze vector (e.g., a direction in which the eye is pointing). The gaze vector along with the position and orientation of the surgeon's head may enable gaze control of a graphical user interface (including a surgical navigation image) displayed on the see-through screen 141. In some embodiments, the surgeon may control the surgical navigation system 100 or components thereof through their gaze using the eye tracker 148 (e.g., moving a cursor of a graphical user interface displayed on transmissive screen 141). FIG. 6B is perspective view of a surgical navigation image based on the eye tracking shown in FIG. 6A. For example, the surgeon in FIG. 6B may select a predetermined function (e.g., highlight anatomy) based on the location (e.g., 1, 2, 3) of their gaze.

Figures 7A, 7B, 7C:
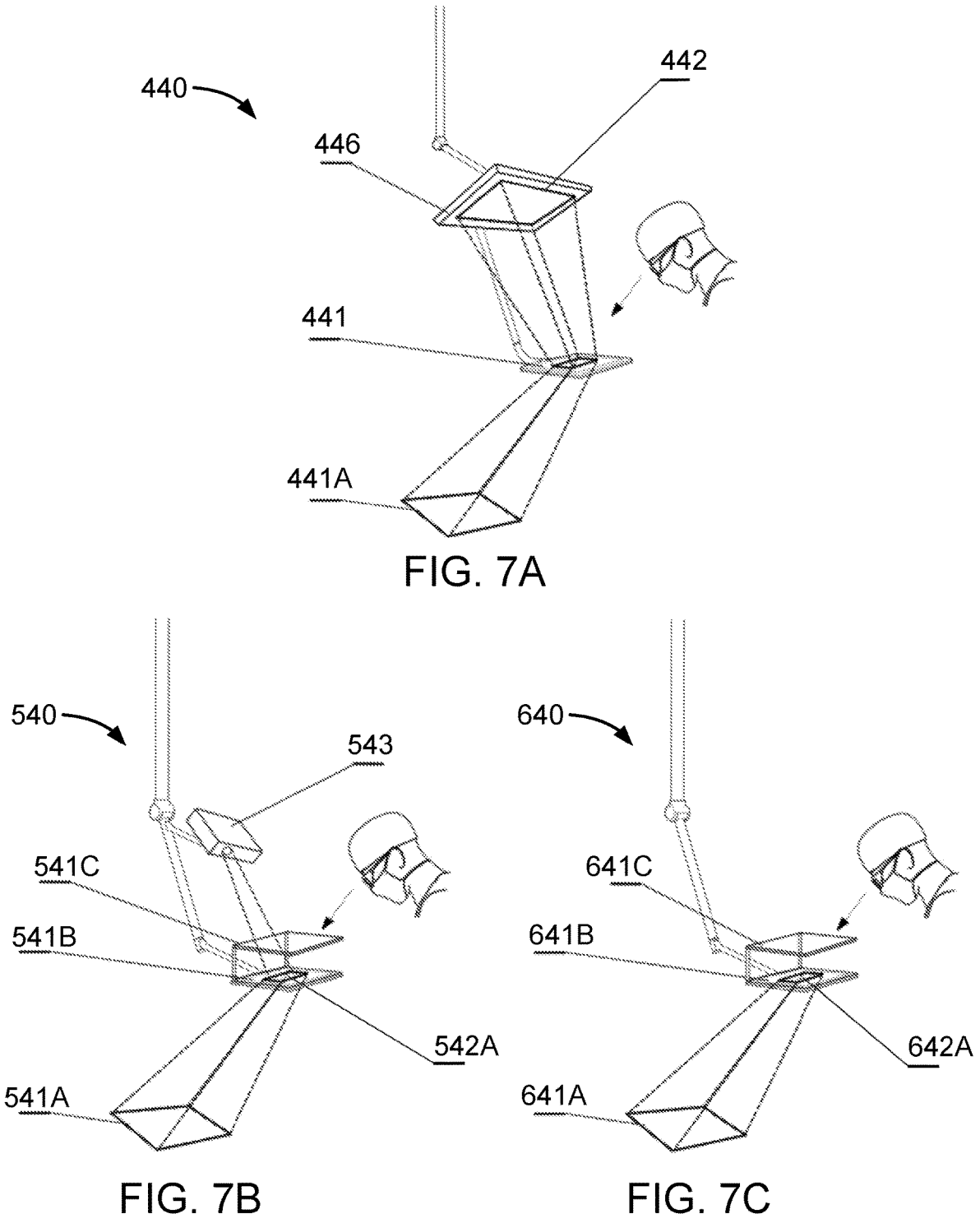
FIGS. 7A-7C are perspective views illustrating a surgeon operating exemplary surgical navigation systems, according to some embodiments.

FIGS. 7A-7C are perspective views illustrating a surgeon operating additional examples of display systems of surgical navigation systems, according to embodiments. Such display systems can be structurally and/or functionally similar to display system 240 or other display systems described herein. As such, certain components of these display systems are not described herein again in detail.

FIG. 7A depicts a surgical navigation system 440 including a stereoscopic three-dimensional display 442, stereoscopic three-dimensional monitor 446, transmissive screen 441, and surgical navigation image 441A. FIG. 7B depicts a surgical navigation system 540 including a stereoscopic three-dimensional projector 543 configured to project surgical navigation images 542A, 541A onto a respective transmissive projection screen 541B and patient anatomy. The partially transmissive and partially reflective projection screen 541B allows the surgeon to simultaneously view the surgical navigation image 542A and a surgical field including patient anatomy. The surgical navigation system 540 may include a lens 541C configured to modify a focal position of the surgical navigation image 542A. FIG. 7C depicts a surgical navigation system 640 including surgical navigation images 642A and 641A projected respectively onto a transmissive projection screen 641B and patient anatomy. The partially transmissive and partially reflective projection screen 641B allows the surgeon to simultaneously view the surgical navigation image 642A and a surgical field including patient anatomy. The surgical navigation system 640 may include a lens 641C configured to modify a focal position of the surgical navigation image 642A. Each of the transmissive screen 441 and projection screens 541B, 641B may be referred to as a see-through visor or see-through screen.

2. Graphical User Interfaces Including Surgical Navigation Images

Figure 8:
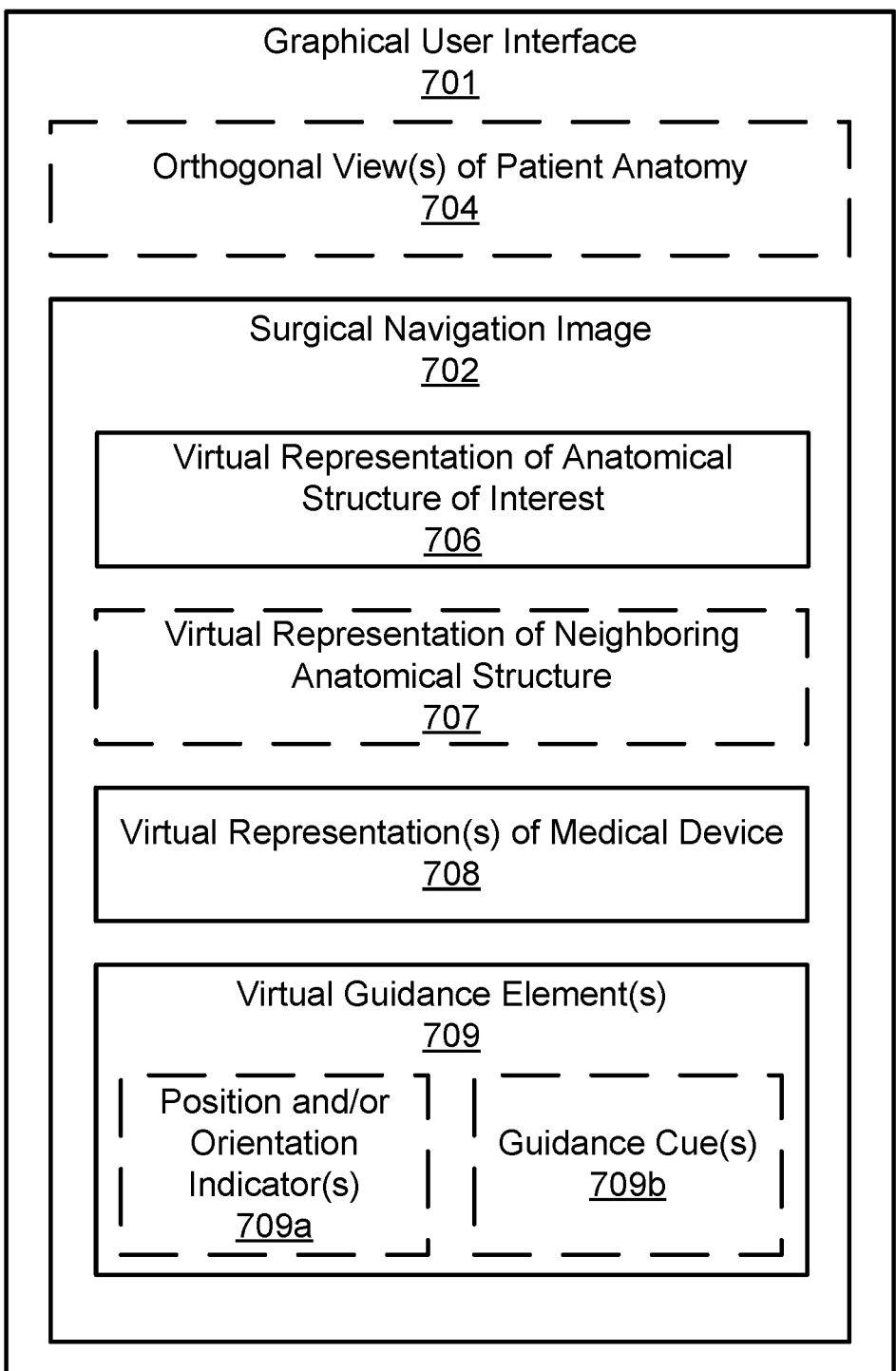
FIG. 8 is a schematic block diagram illustrating a configuration of a graphical user interface including a surgical navigation image, according to some embodiments.

FIG. 8 is a schematic block diagram illustrating a configuration of a graphical user interface 701 including a surgical navigation image 702. The graphical user interface 701 can be generated by a compute device or processor, including, for example, a compute device that is operatively coupled to a display system of a surgical navigation system (e.g., compute device 210) or an onboard processor of the distal system (e.g., a processor of display 242). In some embodiments, a surgical navigation image 702 may include a virtual representation of an anatomical structure of interest 706, a virtual representation of a medical device 708, and a virtual guidance element 709. The virtual guidance element

709 may optionally include one or more of a position and/or orientation indicator 709a associated with a planned position and/or orientation of a medical device and a guidance cue 709b. The surgical navigation image 702 may also optionally include a virtual representation of neighboring anatomical structure 707. In some embodiments, the graphical user interface 701 may optionally include one or more orthogonal view(s) of the patient anatomy 704. Further details of such elements are described with reference to FIGS. 9A-19B below.

While not depicted in FIG. 8, it can be appreciated that other elements can be included in graphical user interface 701. For example, graphical user interface 701 can include a menu with selectable icons, buttons, or other virtual elements. A surgeon or other user can select elements from the menu, e.g., by selecting using an I/O device (e.g., I/O 216, 226) and/or selecting using eye gaze (e.g., as described with reference to FIGS. 6A and 6B).

FIGS. 9A-19B depict various examples of graphical user interfaces including surgical navigation images. As can be understood based on the present disclosure, the graphical user interfaces and surgical navigation images depicted in these figures can be generated by a compute device or processor, including, for example, a compute device that is operatively coupled to a display system of a surgical navigation system (e.g., compute device 210) or an onboard processor of the distal system (e.g., a processor of display 242).

Figure 9A:
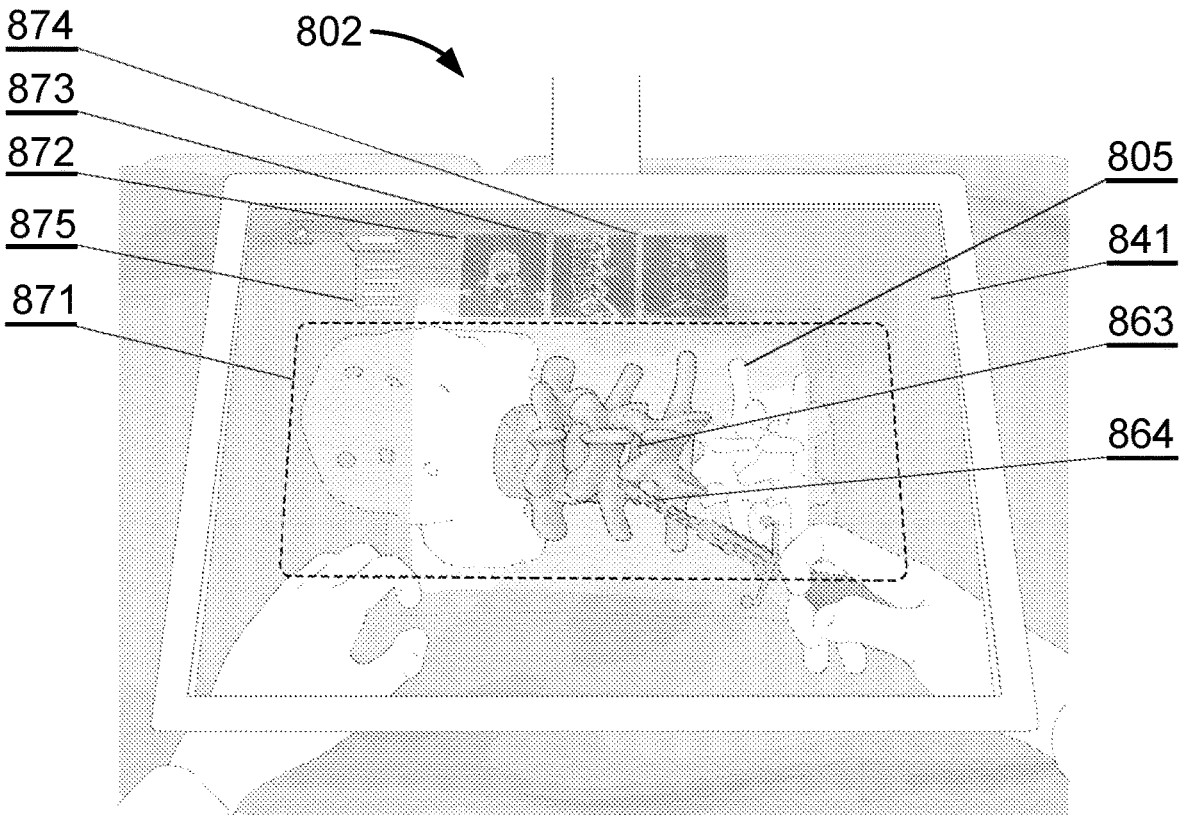
FIGS. 9A and 9B are perspective views illustrating surgical navigation images of a display system, according to some embodiments.
Figure 9B:
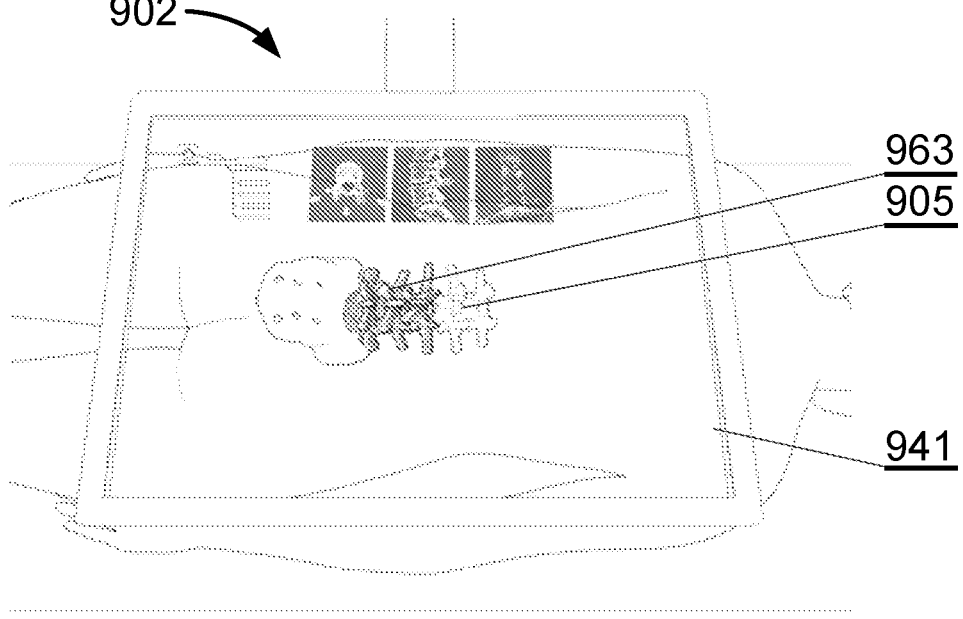

FIGS. 9A and 9B are perspective views illustrating surgical navigation images of a display system. A transmissive screen 802 of a surgical navigation system in FIG. 9A includes a graphical user interface that has a surgical navigation image 841 displayed over (e.g., superimposed on) patient anatomy 805. The surgical navigation image 841 may include a three-dimensional image 871 having virtual representation of patient anatomy 863, a virtual representation of a medical device (e.g., surgical instrument) and/or a virtual guidance element 864 indicating current and planned trajectory and placement of a medical device according to a pre-operative plan. For example, a virtual guidance element 864 may include a suggestion (e.g., prompt) such as for indicating placement of a pedicle screw for spinal surgery and a predetermined (e.g., ideal) orientation of an acetabular component for hip arthroplasty surgery. In some embodiments, the virtual guidance element(s) 864 may include animations and other graphics. The virtual guidance element(s) 864 may be displayed on one or more of the three-dimensional display 871 and the orthogonal planes 872, 873, 874. Virtual guidance element(s) 864 may be used before or during a procedure.

The graphical user interface may further include a menu 875 for control of the surgical navigation system and orthogonal plane images of patient anatomy data including one or more of an axial plane image 872, sagittal plane image 873, and coronal plane image 874. In some embodiments, the orthogonal plane images 872, 873, 874 can be displayed adjacent to the three-dimensional image 871. For example, as shown in FIG. 9A, the three-dimensional image 871 may encompass more than about half of the viewable area of the transmissive screen 802. The transmissive screen 802 further allows a surgeon's hands, surgical instrument, and patient anatomy to be viewed through the transmissive screen 802. In some embodiments, a location of the orthogonal plane images 872, 873, 874 on the transmissive screen 802 may be adjusted in real-time based on the position and/or orientation of the surgeon's head so as to not interfere with the three-dimensional image 871. Therefore, anatomical information of the patient may be projected in three-dimensions on the surgical field and as orthogonal plane images to provide the surgeon an augmented/mixed reality view.

In some embodiments, the surgical navigation system may be stereoscopic such that a wearable device may be a set of 3D glasses configured to stereoscopically view the surgical navigation image 841. In some embodiments, a 3D display of the surgical navigation system may be autostereoscopic such that 3D glasses are not necessary for the surgeon to view the surgical navigation image 841.

As described herein, a surgical navigation image (e.g., image 802) may be generated by an image generator (e.g., compute device 210, image generator 131) based on real-time tracking data (e.g., eye gaze data) generated by a fiducial marker tracker 125. The tracking data can facilitate superposition of virtual representations of patient anatomy and medical devices over the real patient anatomy and medical devices in accordance with the real-time position and/or orientation of one or more of the surgeon's head, the patient anatomy, the surgical instruments, and the medical devices. Accordingly, the image generator can be configured to graphically render a set of virtual objects collocated to the real-world objects according to the surgeon's perspective. For example, the three-dimensional image 871 may be configured to be modified in real-time according to the position and/or orientation of the surgeon's head. The orthogonal plane images 872, 873, 874 may be configured to be modified in real-time according to the position and/or orientation of one or more surgical instruments.

FIG. 9B is a perspective view of surgical navigation image 941 on a transmissive screen 902 depicting collocation of a virtual image of the patient anatomy 963 with real-world patient anatomy 905. It should be appreciated that aligning the line of sight of a surgeon with a see-through mirror with the patient anatomy underneath the see-through mirror, involving the scaling and orientation of the image, can be realized based on known solutions in the field of computer graphics processing, in particular for virtual reality, including virtual scene generation, using mathematical formulas and algorithms related to viewer centered perspective. For example, such solutions are known from various tutorials and textbooks, such as "The Future of the CAVE" by T. A. DeFanti et al., Central European Journal of Engineering, 2010, DOI: 10.2478/s13531-010-0002-5.

Figure 10:
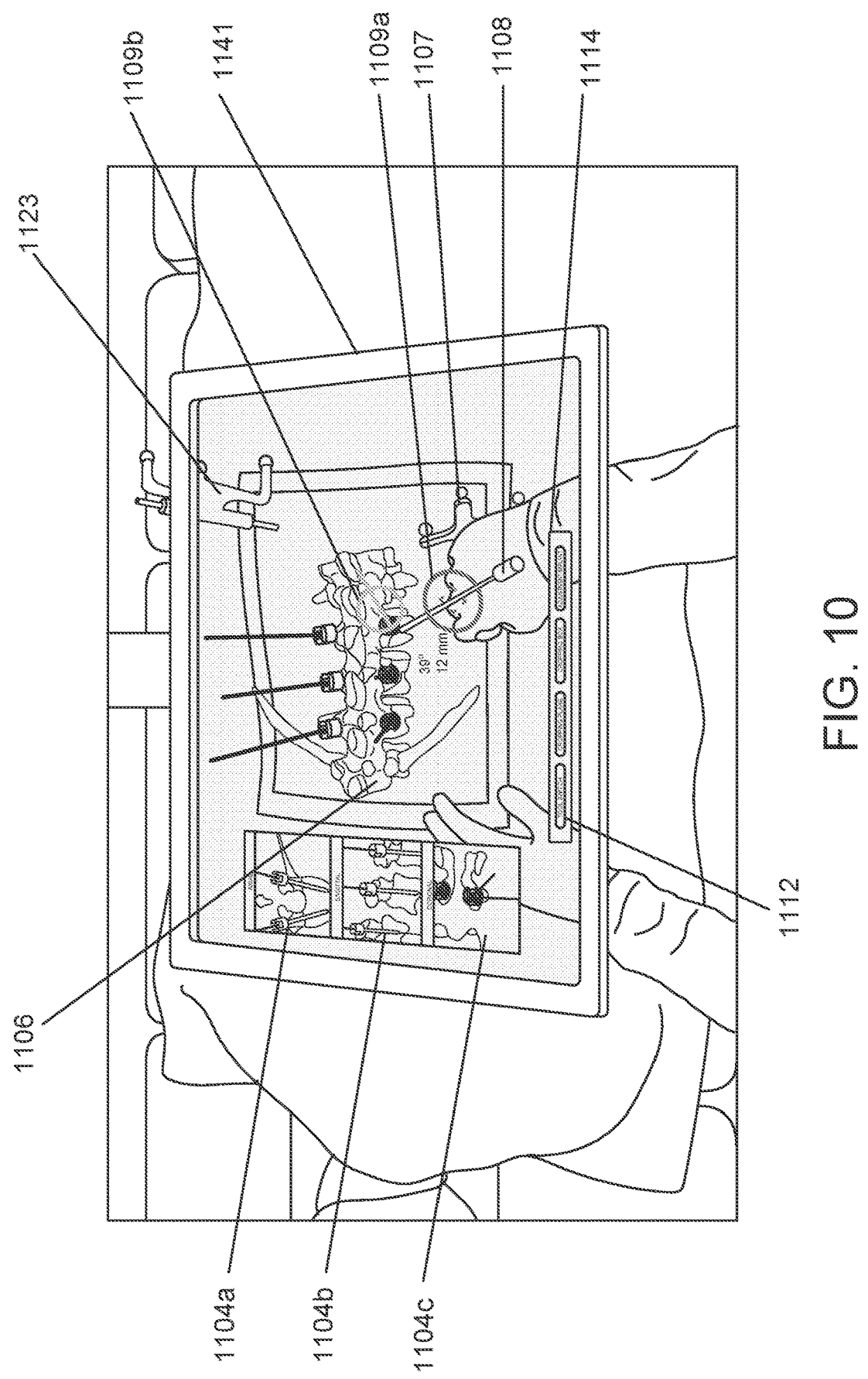
FIG. 10 is a perspective view illustrating a surgical navigation image of a display system, according to some embodiments.

FIG. 10 is a perspective view illustrating a graphical user interface including a surgical navigation image, according to embodiments. In some embodiments, a transmissive screen 1141 of a surgical navigation system includes a surgical navigation image displayed over (e.g., superimposed on) patient anatomy. The surgical navigation image may include a three-dimensional image having virtual representation of patient anatomy 1106, a virtual representation of a medical device 1108 (e.g., surgical instrument), and/or a virtual guidance element 1109*a*, 1109*b* indicating current and planned trajectory and placement of a medical device according to a pre-operative plan. For example, a virtual guidance element 1109*a* may include a suggestion (e.g., prompt) such as for indicating placement of a pedicle screw for spinal surgery. In some embodiments, the virtual guidance element(s) 1109*a* may include animations and other graphics. The virtual guidance element(s) 1109*a*, 1109*b* may be displayed on the transmissive screen 1141. One or more of the actual patient anatomy, surgical instrument 1107, 1123, and surgeon 1114 may be visible through the transmissive screen 1141.

The orthogonal plane images of patient anatomy data can include one or more of an axial plane image 1104*a*, sagittal plane image 1104*b*, and coronal plane image 1104*c*. In some embodiments, the orthogonal plane images 1104*a*-1104*c* can be displayed adjacent to the virtual representations of patient anatomy 1106. The virtual guidance element(s) 1109*a*, 1109*b* may be displayed on the orthogonal plane images 1104*a*, 1104*b*, 1104*c*.

In some embodiments, the transmissive screen 1141 may further display a menu 1112 for control of the surgical navigation system and may include functions including, but not limited to, tool switch, cropping plane, cropping box, and adjust implant. In some embodiments, the menu 1112 elements can be selected by the surgeon by tapping the see-through screen at the location where the elements are shown to the surgeon. Alternatively or additionally, the menu 1112 elements can be selected by the surgeon based on the eye gaze of the surgeon (e.g., as detected via the process described in FIGS. 6A-6B).

Figure 11A:
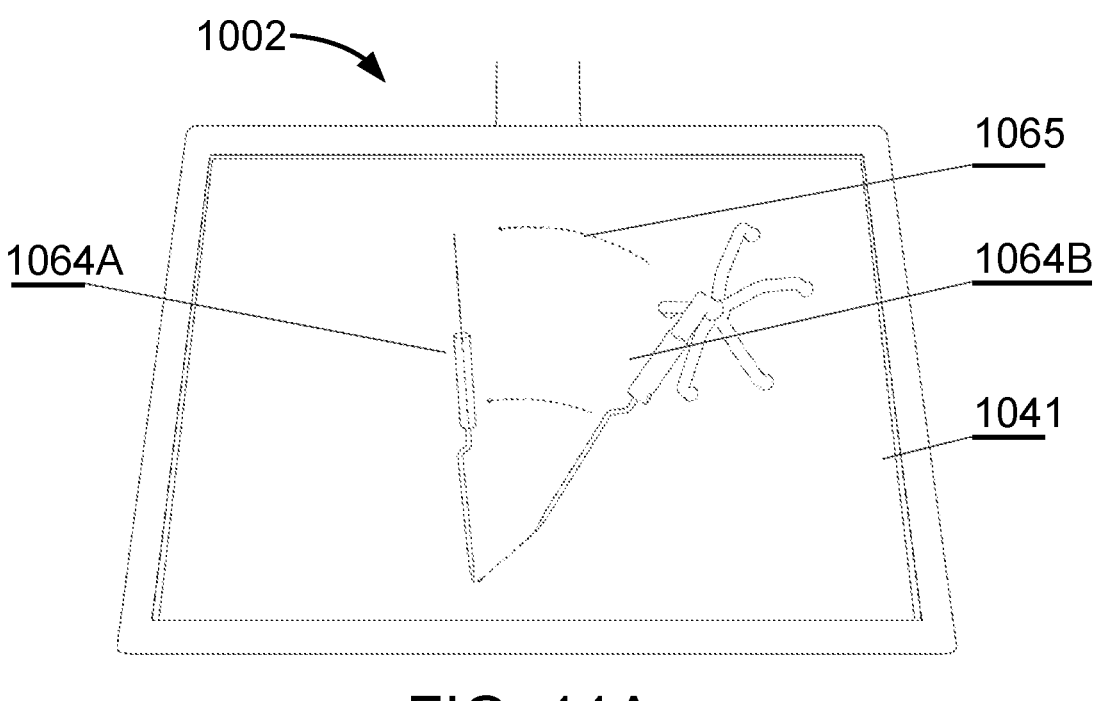
FIGS. 11A-11C are perspective views illustrating surgical navigation images of a display system, according to some embodiments.
Figure 11B:
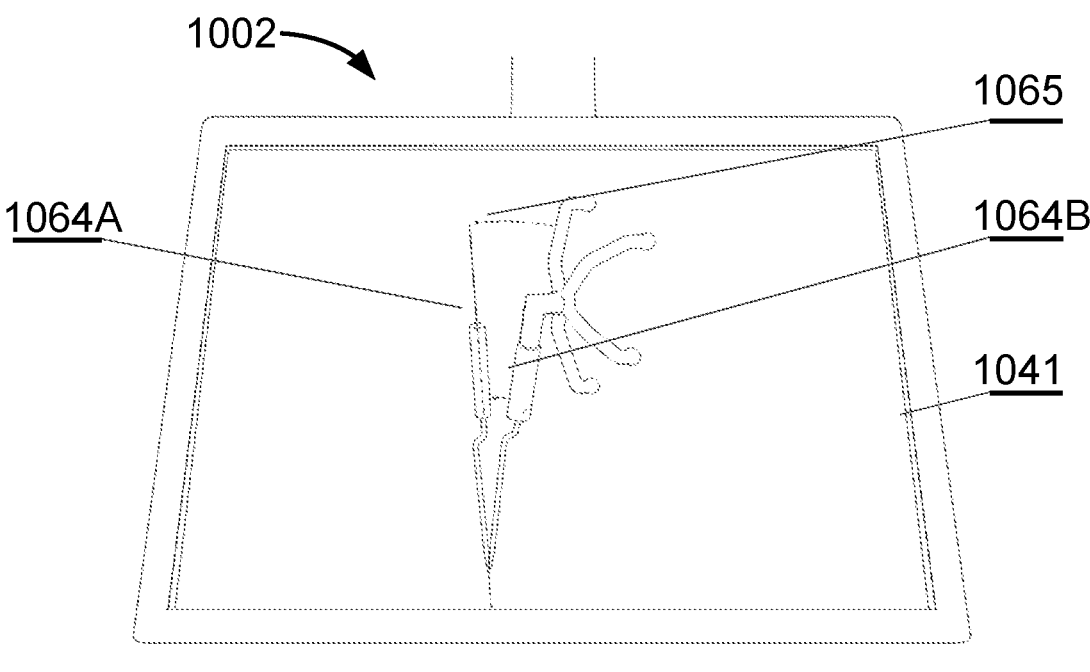
Figure 11C:
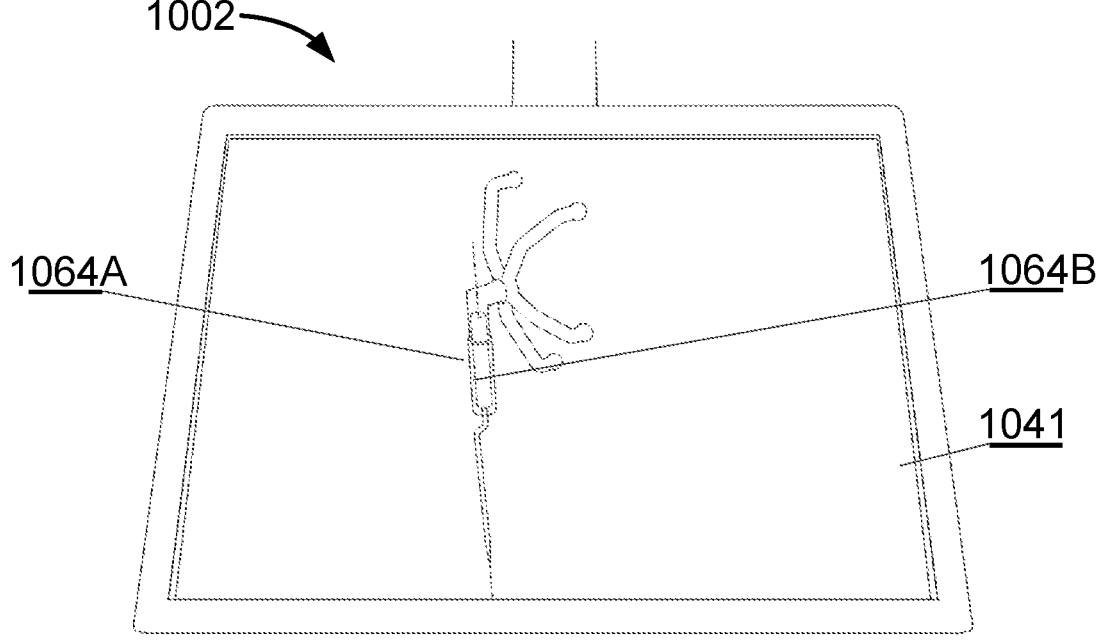

FIGS. 11A-11C are perspective views illustrating surgical navigation images shown on a transmissive screen 1041 of a display system. In some embodiments, a surgical image generator (e.g., surgical image generator 131) may be configured to generate a surgical navigation image 1002 including data representing simultaneously a first virtual image 1064A (e.g., one or more position and/or orientation indicators) and a second virtual image 1064B (e.g., one or more position and/or orientation indicators). The first virtual image 1064A of a surgical instrument can indicate a planned position and/or orientation of the surgical instrument according to an operative plan data 161, 162, which may be manually defined by the surgeon or suggested by the system, e.g., based on a preoperative or intraoperative plan. For example, the first virtual image may include a first indicator (e.g., geometric shape) located in a position corresponding to the planned position and/or orientation of the surgical instrument.

The second virtual image 1064B of the surgical instrument can correspond to the current position and/or orientation of the surgical instrument based on the current relative position and/or orientation of the surgeon's head, the transmissive screen 1041, the patient anatomy, and the surgical instrument. For example, the second virtual image may include a second indicator (e.g., geometric shape) located in a position corresponding to the current/live position and/or orientation of the surgical instrument. Additionally or alternatively, the surgical navigation image may further be based on a patient anatomy scan 163 which can be generated before or during a procedure.

FIG. 11A illustrates a difference between the first virtual image 1064A corresponding to a planned position and/or orientation of the surgical instrument and the current/live position and/or orientation of the surgical instrument visible as the real surgical instrument via the transmissive screen 1041 and/or the second virtual image 1064B corresponding to laid over the current position of the surgical instrument. In some embodiments, one or more graphical guidance elements 1065 (e.g., guidance cues, lines, arrows) may indicate a change to move (e.g., direction of motion) the position and/or orientation of the actual or real surgical instrument to the planned position and/or orientation. For example, a graphical cue may indicate the required change of position and orientation of the surgical instrument to match the planned position and orientation according to the pre-operative plan data.

FIG. 11B illustrates a tip of the planned position and/or orientation of the surgical instrument that matches the position of the actual or real tip of the visible surgical instrument and/or displayed as the second virtual image 1064B. However, the orientation and other portions of the surgical instrument do not match between the planned position and/or orientation and the visible surgical instrument and/or second virtual image 1064B. In some embodiments, the system may provide additional guidance elements (e.g., guidance cues, information) to facilitate matching between the planned position and/or orientation and the actual or real surgical instrument.

FIG. 11C illustrates a match (e.g., overlap) between the planned position and/or orientation of the surgical instrument and the actual visible surgical instrument and/or second virtual image 1064B. In FIG. 11C, guidance elements are no longer displayed, but one or more of the virtual images 1064A, 1064B may be modified to indicate successful matching (e.g., highlighting, color change, line change, pattern change, blinking). In some embodiments, the first indicator may overlap the second indicator. For example, the center of the first geometric shape may overlap with the center of the second geometric shape. According to another embodiment, the visual confirmation of alignment may comprise a change in at least one of shape, size, pattern, line, or color of the first and/or second indicator.

In some embodiments, the first indicator may include a set of peripherical markers (e.g., graphical indicia) located at a periphery of the first indicator. In some embodiments, the second indicator may include a set of center markers (e.g., graphical indicia) located at a center of the second indicator.

In some embodiments, the first geometric shape may have a main plane (e.g., lie or substantially lie within a plane) perpendicular to a longitudinal axis of the surgical instrument in the planned position and/or orientation, and the second geometric shape may have a main plane (e.g., lie or substantially lie within a plane) perpendicular to a longitudinal axis of the surgical instrument in the current position and/or orientation. In some embodiments, one or more of the size, pattern, line, and color of the second geometric shape may change depending on a discrepancy of the current position and/or orientation of the surgical instrument from the planned position and/or orientation of the surgical instrument.

The surgical navigation system may further comprise an audible indicator of the current position and/or orientation of the surgical instrument relative to the planned position and/or orientation of the surgical instrument. For example, a first audible indicator can correspond to a proximity of a location of the current position of the surgical instrument to the planned position of the surgical instrument. A second audible indicator can correspond to the current angular orientation of the surgical instrument relative to the planned angular orientation of the surgical instrument. In some embodiments, the first audible indicator may be different than the second audible indicator. For example, the first and/or second audible indicator may change as the current position and orientation of the surgical instrument gets closer to or farther away from the planned position and/or orientation of the surgical instrument.

In some embodiments, the first and/or second audible indicators may change in at least one of tempo, pitch, and intensity. For example, the first and/or second audible indicator may increase in tempo as the current position and/or orientation of the surgical instrument moves closer to alignment with the planned position and/or orientation and decrease in tempo as the current position and/or orientation moves farther out of alignment with the planned position and/or orientation. In some embodiments, the change in the first and/or second audible indicators occurs simultaneously with changes in at least one of the first or second visual indicators as at least one of the current position and/or orientation of the surgical instruments moves closer to or farther away from at least one of the planned position and/or orientation, respectively, of the surgical instrument.

Figures 12A, 12B, 12C:
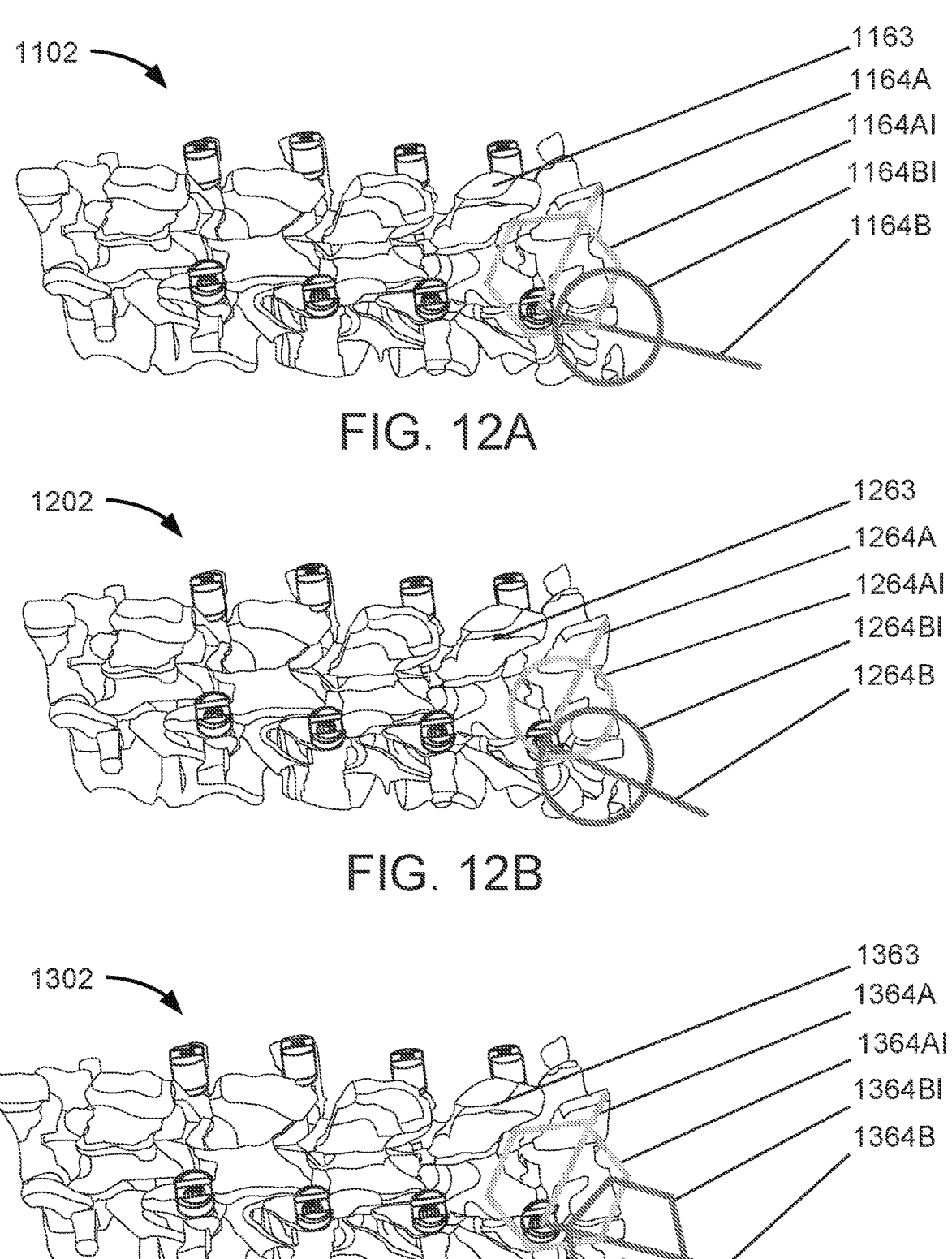
FIGS. 12A-12E are surgical navigation images, according to some embodiments.

FIGS. 12A-12E are illustrative surgical navigation images, according to additional embodiments. FIG. 12A depicts surgical navigation image 1102 based on patient anatomy data 1163 and includes a first virtual image 1164A and a second virtual image 1164B. The first virtual image 1164A can include a first indicator 1164AI corresponding to a planned position and/or orientation of a surgical instrument, and the second virtual image 1164B can include a second indicator 1164BI corresponding to a current position and/or orientation of the surgical instrument. The first indicator 1164AI can be a first geometric shape located in a position corresponding to the planned position and/or orientation of the surgical instrument. Similarly, the second indicator 1164BI can be a second geometric shape located in a position corresponding to the current position and/or orientation of the surgical instrument. In FIG. 12A, the first indicator 1164AI may be a hexagon having a first color, and the second indicator 1164BI may be a circle having a second color different from the first color, although it should be appreciated that the first and second indicators may have the same or different shapes.

In some embodiments, the first geometric shape may have a main plane substantially perpendicular to a longitudinal axis of the surgical instrument in the planned position and/or orientation. The second geometric shape may have a main plane substantially perpendicular to a longitudinal axis of the surgical instrument in the current position and/or orientation. The geometric shapes described herein may be one or more of a 2D shape (e.g., circle, oval, triangle, rectangle, rhombus, pentagon, hexagon) and 3D shape (e.g., sphere, cube, cone, pyramid, cylinder).

FIG. 12B depicts surgical navigation image 1202 based on patient anatomy data 1263 and includes a first virtual image 1264A and a second virtual image 1264B. The first virtual image 1264A can include a first indicator 1264AI corresponding to a planned position and/or orientation of a surgical instrument, and the second virtual image 1264B can include a second indicator 1264BI corresponding to a current position and/or orientation of the surgical instrument. The first indicator 1264AI can be a first geometric shape located in a position corresponding to the planned position and/or orientation of the surgical instrument. Similarly, the second indicator 1264BI can be a second geometric shape located in a position corresponding to the current position and/or orientation of the surgical instrument. In FIG. 12B, the first indicator 1264AI may be a circle having a first color, and the second indicator 1264BI may be a circle having a second color different from the first color.

FIG. 12C depicts surgical navigation image 1302 based on patient anatomy data 1363 and includes a first virtual image 1364A and a second virtual image 1364B. The first virtual image 1364A can include a first indicator 1364AI corresponding to a planned position and/or orientation of a surgical instrument, and the second virtual image 1364B can include a second indicator 1364BI corresponding to a current position and/or orientation of the surgical instrument. The first indicator 1364AI can be a first geometric shape located in a position corresponding to the planned position and/or orientation of the surgical instrument. Similarly, the second indicator 1364BI can be a second geometric shape located in a position corresponding to the current position and/or orientation of the surgical instrument. In FIG. 12C, the first indicator 1364AI may be a hexagon having a first color, and the second indicator 1364BI may be a hexagon having a second color different from the first color.

Figures 12D, 12E:
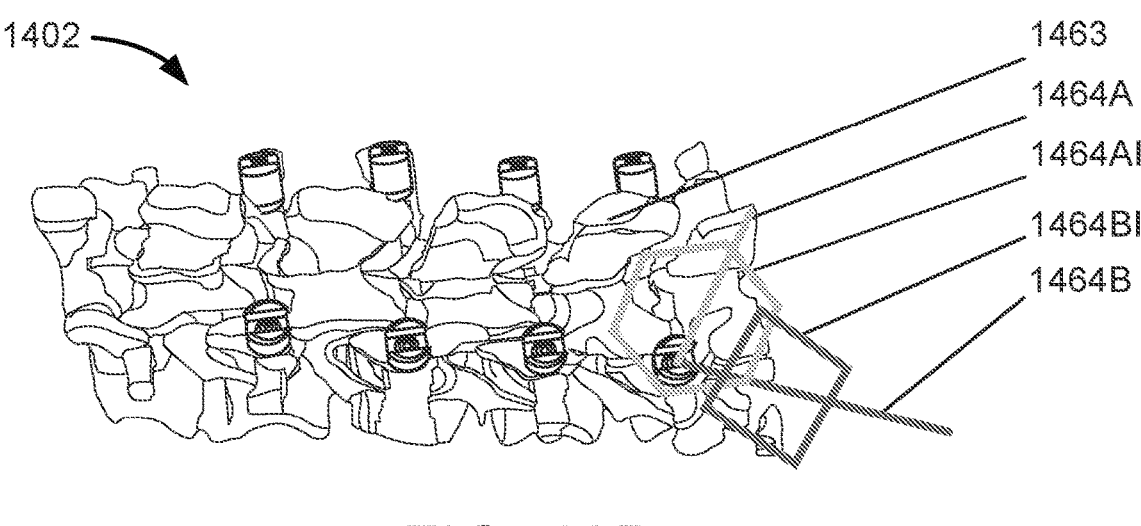

FIG. 12D depicts surgical navigation image 1402 based on patient anatomy data 1463 and includes a first virtual image 1464A and a second virtual image 1464B. The first virtual image 1464A can include a first indicator 1464AI corresponding to a planned position and/or orientation of a surgical instrument, and the second virtual image 1464B can include a second indicator 1464BI corresponding to a current position and/or orientation of the surgical instrument. The first indicator 1464AI can be a first geometric shape located in a position corresponding to the planned position and/or orientation of the surgical instrument. Similarly, the second indicator 1464BI can be a second geometric shape located in a position corresponding to the current position and/or orientation of the surgical instrument. In FIG. 12D, the first indicator 1464AI may be a hexagon having a first color, and the second indicator 1464BI may be a square having a second color different from the first color.

FIG. 12E depicts surgical navigation image 1502 based on patient anatomy data 1463 and includes a first virtual image 1464A and a second virtual image 1464B. The first virtual image 1464A can include a first indicator 1464AI corresponding to a planned position and/or orientation of a surgical instrument, and the second virtual image 1464B can include a second indicator 1464BI corresponding to a current position and/or orientation of the surgical instrument. The first indicator 1464AI can be a first geometric shape located in a position corresponding to the planned position and/or orientation of the surgical instrument. Similarly, the second indicator 1464BI can be a second geometric shape located in a position corresponding to the current position and/or orientation of the surgical instrument. In FIG. 12E, the first indicator 1464AI may be a hexagon having a first color, and the second indicator 1464BI may be a triangle having a second color different from the first color.

It can be appreciated that the first and second indicators, as described with reference to FIGS. 12A-12E, can be or include any suitable visual shape, feature, characteristic, etc. While not depicted in FIGS. 12A-12E, it can be appreciated that these first and second indicators can rotate (e.g., a triangle, a pentagon, an oval, etc. can rotate) to correspond to when a surgeon has rotated the surgical instrument. Such rotation can serve to further guide the surgeon in moving the surgical instrument from its current position and orientation to its planned position or orientation.

Figure 13A:
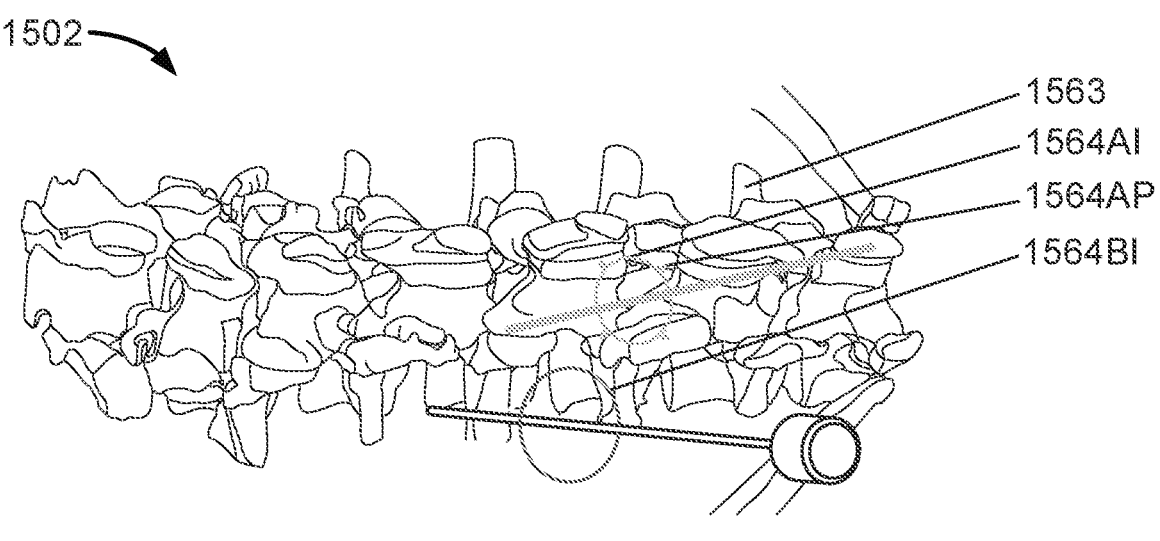
FIGS. 13A and 13B are surgical navigation images, according to some embodiments.
Figure 13B:
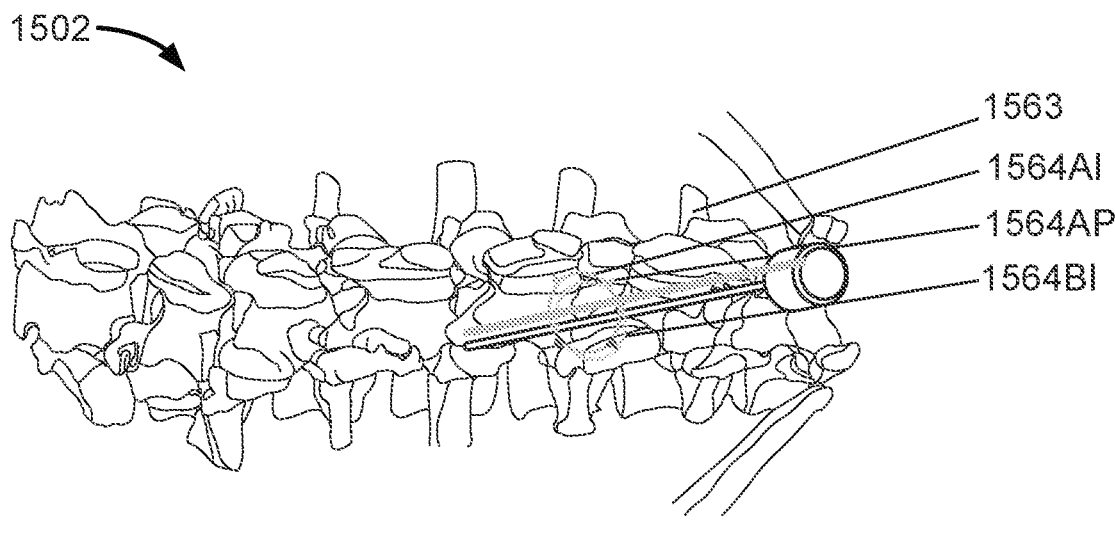

FIGS. 13A and 13B are surgical navigation images 1502 based on patient anatomy data 1563 and includes a first virtual image having a first indicator 1564AI corresponding to a planned position and/or orientation of a surgical instrument, and a second virtual image having a second indicator 1564BI corresponding to a current position and/or orientation of the surgical instrument. The first indicator 1564AI can be a first geometric shape located in a position corresponding to the planned position and/or orientation of the surgical instrument. The first indicator 1564AI may include a peripheral marker 1564AP (e.g., graphical indicia) located at a periphery of the first indicator 1564AI. The graphical indicia of the peripherical markers 1564AP may have a form of short lines, triangles, or other geometric shapes. The second indicator 1564BI can be a second geometric shape located in a position corresponding to the current position and/or orientation of the surgical instrument. In FIG. 13A, the first indicator 1564AI may be a circle having a first color, and the second indicator 1564BI may be a circle having a second color different from the first color.

As the surgical instrument moves towards a planned position and/or orientation as shown from FIG. 13A to FIG. 13B, the second indicator 1564BI moves towards the first indicator 1664AI. When the surgical instrument moves within a threshold range from the planned position and/or orientation (e.g., due to overlap between the first and second indicators), the pattern, thickness, and/or color of the second indicator 1564BI may change, e.g., from being darker and solid (e.g., red) in FIG. 13A to being lighter and dashed (e.g., white) in FIG. 13B. This change can signify or indicate to a surgeon that the surgeon's manipulation of the surgical instrument is moving the surgical instrument closer to its planned position and/or orientation. In some embodiments, once the surgical instrument is closer to its planned position and orientation, the peripheral markers 1564AP can also change color, shape, or other characteristic to guide the surgeon in positioning and/or orientating the surgical instrument. For example, the peripheral markers 1564AP in FIG. 13A can be a first color (e.g., green) when the surgical instrument is not yet near its planned position and orientation. In FIG. 13B, the peripheral markers 1564AP can include two lower markers that are a different color from two upper markers. The two lower markers can be located on a side of the first indicator 1564AI that is closer to the current position of the surgical instrument (e.g., a center of the second indicator 1564BI). The color difference can be used to signify or indicate to the surgeon that the surgical instrument needs to be moved upward relative to the bottom peripheral markers such that the second indicator 1564BI associated with the current position and orientation of the surgical instrument aligns with the first indicator 1564AI associated with the planned position and orientation of the surgical instrument. As such, the peripheral markers can functional as directional markers that can indicate to a surgeon the direction to move the surgical instrument for aligning the current position and orientation of the surgical instrument with the planned position and orientation of the surgical instrument.

It can be appreciated that the degree of alignment between the current position and/or orientation of the surgical instrument (or other medical device) and its planned position and/or orientation can be assessed based on one or more criteria. For example, in some embodiments, the difference between the current and planned positions and/or orientations can be measured based on a degree of overlap between the first indicator associated with the planned position and orientation and the second indicator associated with the current position and orientation. In such cases, when the degree of overlap is greater than a predefined threshold value or within a predefined threshold range, this can trigger a change in color or other characteristic of one or both of the first and second indicators. Alternatively, the degree of alignment between the current and planned positions and/or orientations can be measured based on (1) a difference between the current position and the planned position of the surgical instrument and/or (2) a difference between the current orientation and the planned orientation of the surgical instrument. This difference can be evaluated in values or percentages. For example, when the difference between the current position and the planned position of the surgical instrument and the difference between the current orientation and the planned orientation of the surgical instrument is less than a predefined value and/or different from one another by a predefined percentage, then this can trigger a change in color or other characteristic of one or both of the first and second indicators. Other suitable methods or criteria for measuring the alignment between the current and planned positions and/or orientations of the surgical instrument can also be used without departing from the scope of the present disclosure.

Figures 14A, 14B, 14C:
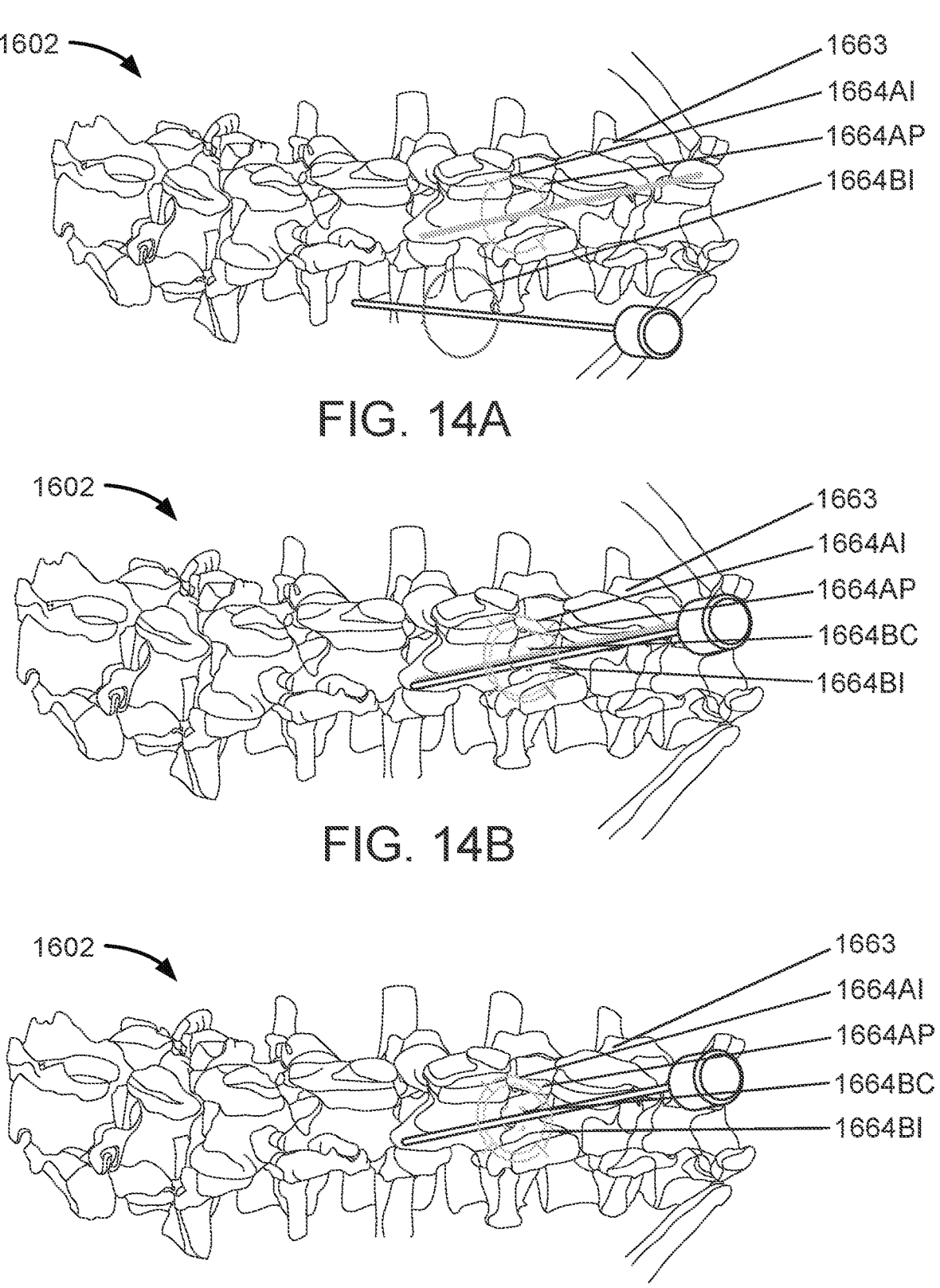
FIGS. 14A-14C are surgical navigation images, according to some embodiments.

FIGS. 14A-14C are surgical navigation images 1602 based on patient anatomy data 1663 and includes a first virtual image having a first indicator 1664AI corresponding to a planned position and/or orientation of a surgical instrument, and a second virtual image having a second indicator 1664BI corresponding to a current position and/or orientation of the surgical instrument. The first indicator 1664AI can be a first geometric shape located in a position corresponding to the planned position and/or orientation of the surgical instrument. The first indicator 1664AI may include a set of peripheral markers 1664AP (e.g., graphical indicia) located at a periphery of the first indicator 1664AI. The graphical indicia of the peripherical markers 1664AP may have a form of short lines or other geometric shapes. The second indicator 1664BI can be a second geometric shape located in a position corresponding to the current position and/or orientation of the surgical instrument. In FIG. 14A, the first indicator 1664AI may be a circle having a first color, and the second indicator 1664BI may be a circle having a second color different from the first color. As the surgical instrument moves towards a planned position and/or orientation as shown from FIG. 14A to FIG. 14B and FIG. 14C, the second indicator 1664BI moves towards the first indicator 1664AI.

In some embodiments, the second indicator 1664BI may include a set of center markers 1664BC (e.g., graphical indicia), as shown in FIG. 14B, located about a center of the second indicator 1664BII. For example, the set of center markers 1664BC may be displayed when the first indicator 1664AI and second indicator 1664BI align by a predetermined amount (e.g., overlap by a threshold amount or percentage). Furthermore, one or more of the first indicator 1664AI, set of peripheral markers 1664AP, second indicator 1664BI, and set of center markers 1664BC may appear and/or change in one or more of shape, size, color, or other characteristics as the planned and current positions and/or orientations of the surgical instrument move towards alignment based on a predetermined threshold. For example, as shown in FIG. 14C, each of the first indicator 1664AI, set of peripheral markers 1664AP, second indicator 1664BII, and set of center markers 1664BC may change to be the same shape, size, and color when the planned and current position and/or orientation of the surgical instrument substantially aligns. As depicted in FIG. 14B, the set of center markers 1664BI may include the vertices of a square, which marks in greater precision the planned position and/or orientation of the surgical instrument. In this manner, the first indicator 1664AI and of the second indicator 1664BI may facilitate navigation of a surgical instrument to the planned position and/or orientation.

Figure 15A:
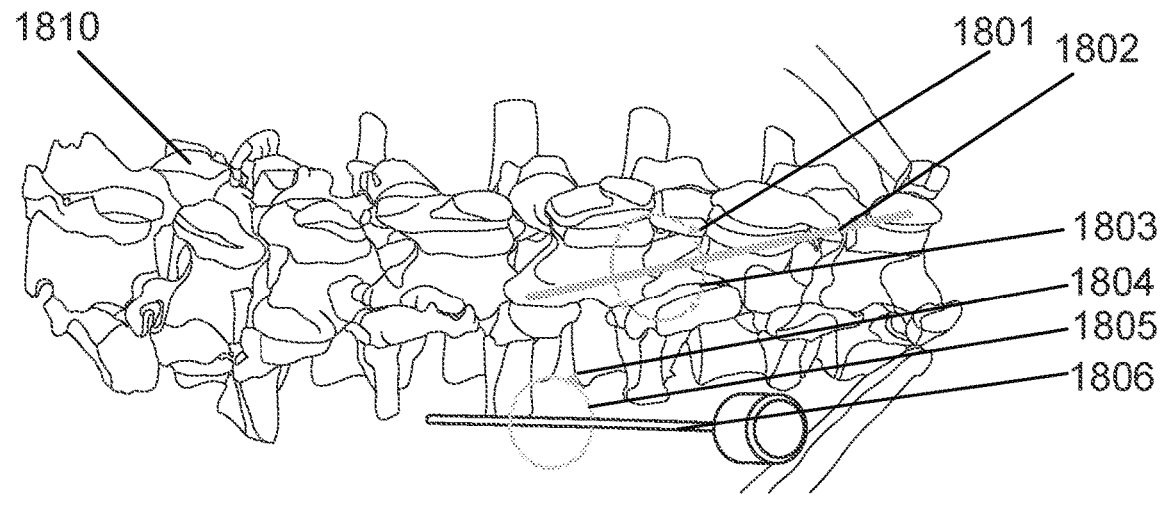
FIGS. 15A-15C are surgical navigation images, according to some embodiments.
Figure 15B:
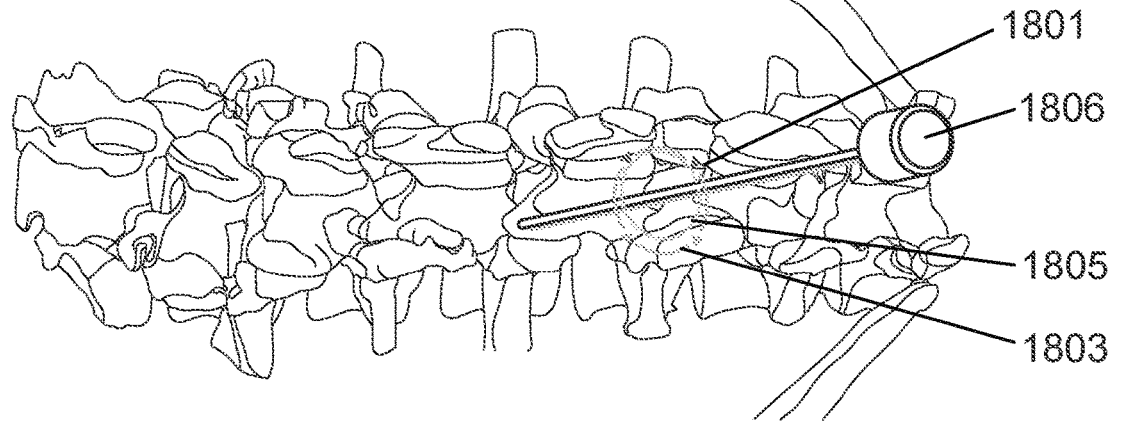
Figure 15C:
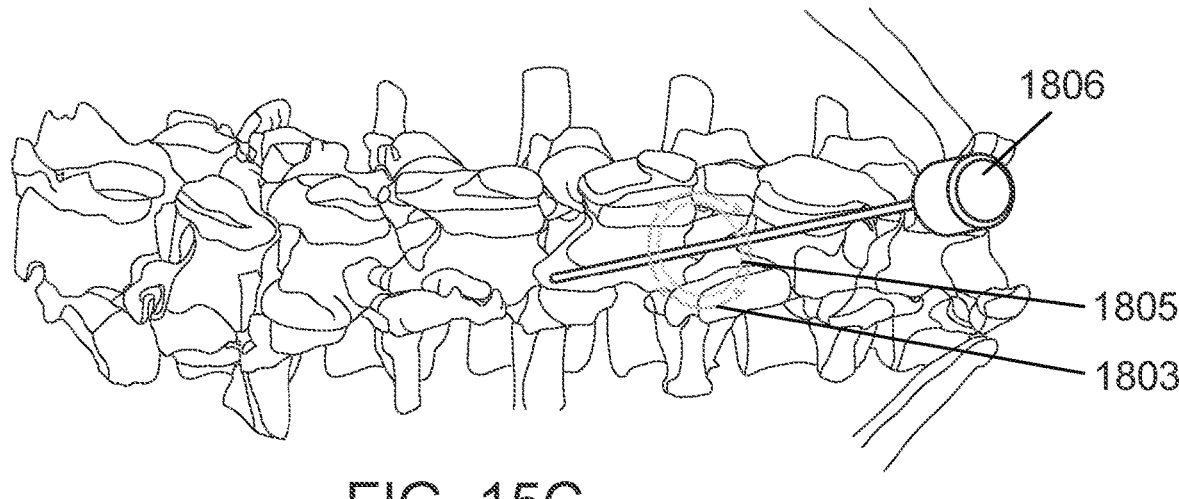

FIGS. 15A-15C are surgical navigation images 1810 including a first virtual image 1802 having a first indicator 1803 corresponding to a planned position and/or orientation of a surgical instrument, and a second virtual image 1806 having a second indicator 1805 corresponding to a current position and/or orientation of the surgical instrument. The first indicator 1803 can be a first geometric shape located in a position corresponding to the planned position and/or orientation of the surgical instrument. The first indicator 1803 may include a set of peripheral markers 1801 (e.g., triangles along a circumference of a circle) located at a periphery of the first indicator 1803. For example, the set of peripheral markers 1801 may point towards a center of the virtual instrument in the planned position and/or orientation. The second indicator 1805 can be a second geometric shape located in a position corresponding to the current position and/or orientation of the surgical instrument. The second indicator 1805 may include a set of peripheral markers 1804 (e.g., triangle along a circumference of a circle) pointing toward the first virtual image 1802.

In FIG. 15B, the second virtual image 1806 is brought close to alignment with the first virtual image 1802 such that the set of peripheral markers 1804 may disappear. One or more of the first indicator 1803 and set of peripheral markers 1801 may change in color or other characteristics, and the second indicator 1805 may be enclosed by the first indicator 1803. FIG. 15C depicts the substantial alignment (e.g., overlap) between the second virtual image 1806 and the first virtual image 1802.

Figure 16A:
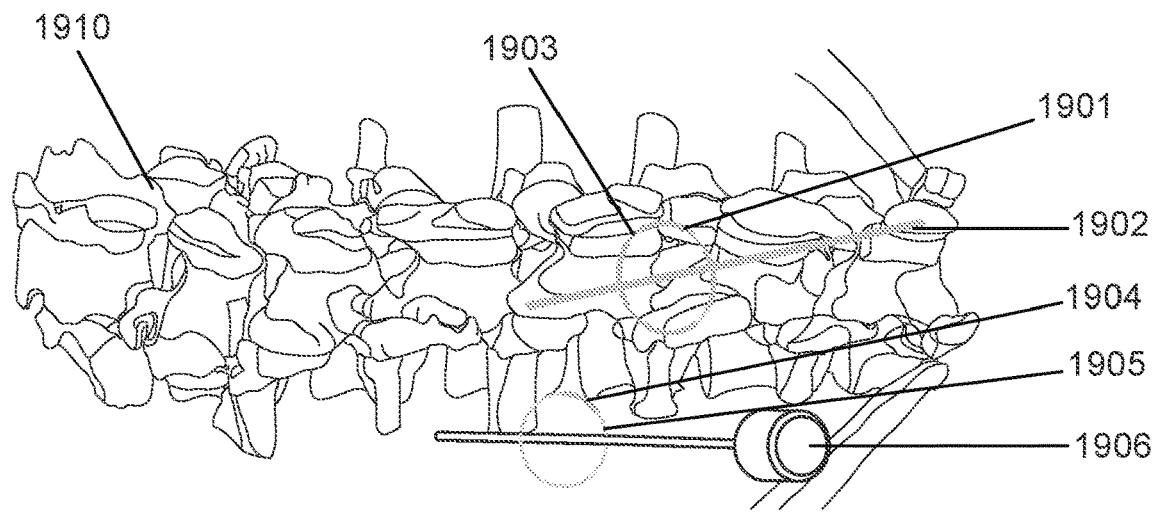
FIGS. 16A-16C are surgical navigation images, according to some embodiments.
Figure 16B:
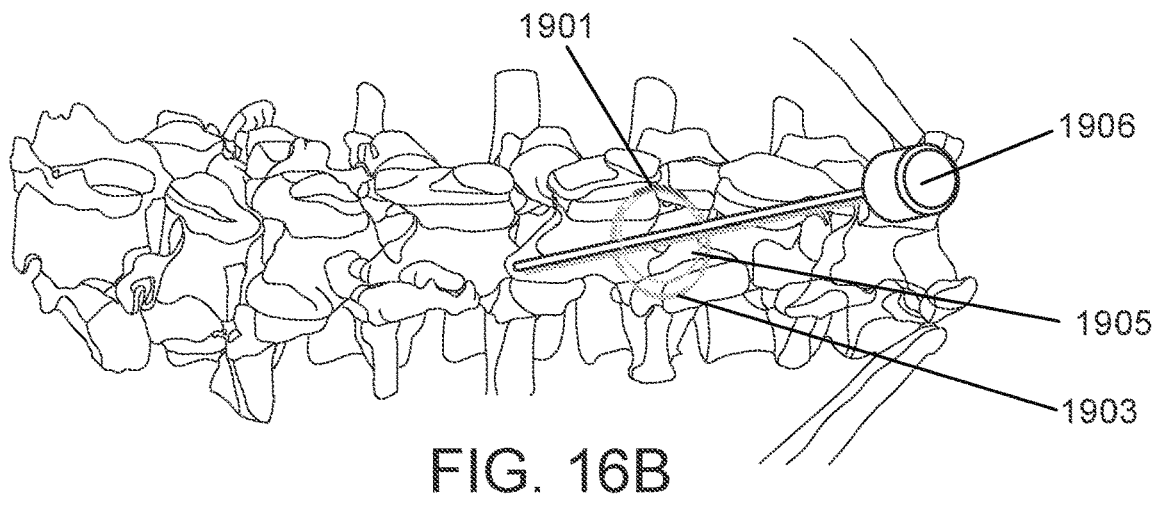
Figure 16C:
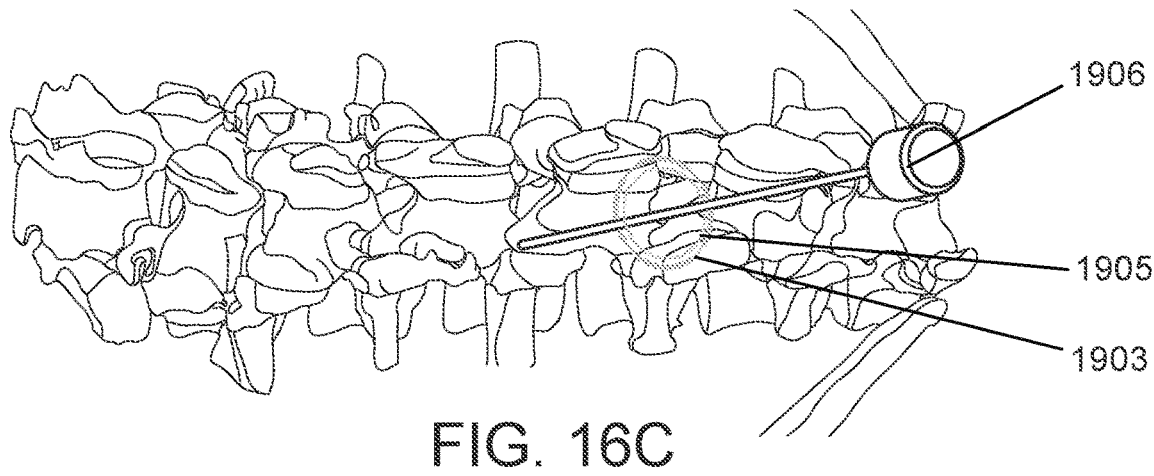

In some embodiments, one or more peripheral indicators can be represented using lines with different characteristics (e.g., colors, thickness, etc.). FIGS. 16A-16C are surgical navigation images 1910 including a first virtual image 1902 having a first indicator 1903 corresponding to a planned position and/or orientation of a surgical instrument, and a second virtual image 1906 having a second indicator 1905 corresponding to a current position and/or orientation of the surgical instrument. The first indicator 1903 can be a first geometric shape located in a position corresponding to the planned position and/or orientation of the surgical instrument. The first indicator 1903 may include a set of peripheral markers 1901, such as, for example, portions of the circle having a different color and/or thickness to the first indicator 1903. As depicted in FIG. 16A, the peripheral markers 1901 can be sections of the first indicator 1903 that are shown with a thicker line. The second indicator 1905 can be a second geometric shape located in a position corresponding to the current position and/or orientation of the surgical instrument. The second indicator 1905 may include a set of peripheral markers 1904 that is positioned closer to the first virtual image 1902. The positioning of the second set of peripheral markers 1904 can indicate a directionality toward the first virtual image 1902. In particular, the set of peripheral markers 1904 can be a section of the second indicator 1905 that is a different color than the remaining sections of the second indicator 1905. As shown in FIG. 16A, the set of peripheral markers 1904 includes a green section of the second indicator 1905.

In FIG. 16B, the second virtual image 1906 is brought close to alignment with the first virtual image 1902 such that the set of peripheral markers 1904 may disappear. However, one or more of the first indicator 1903 and set of peripheral markers 1901 may change in color, and the second indicator 1905 may be enclosed by the first indicator 1903. For example, in FIG. 16B, one of the peripheral indicators 1901 has changed color to a second color (e.g., a darker color or red) to indicate to a surgeon that the current position and/or orientation of the surgical instrument deviates from the planned location and/or orientation of the surgical instrument in the direction that has changed color. FIG. 16C depicts the substantial alignment (e.g., overlap) between the second virtual image 1906 and the first virtual image 1902.

Figures 17A, 17B:
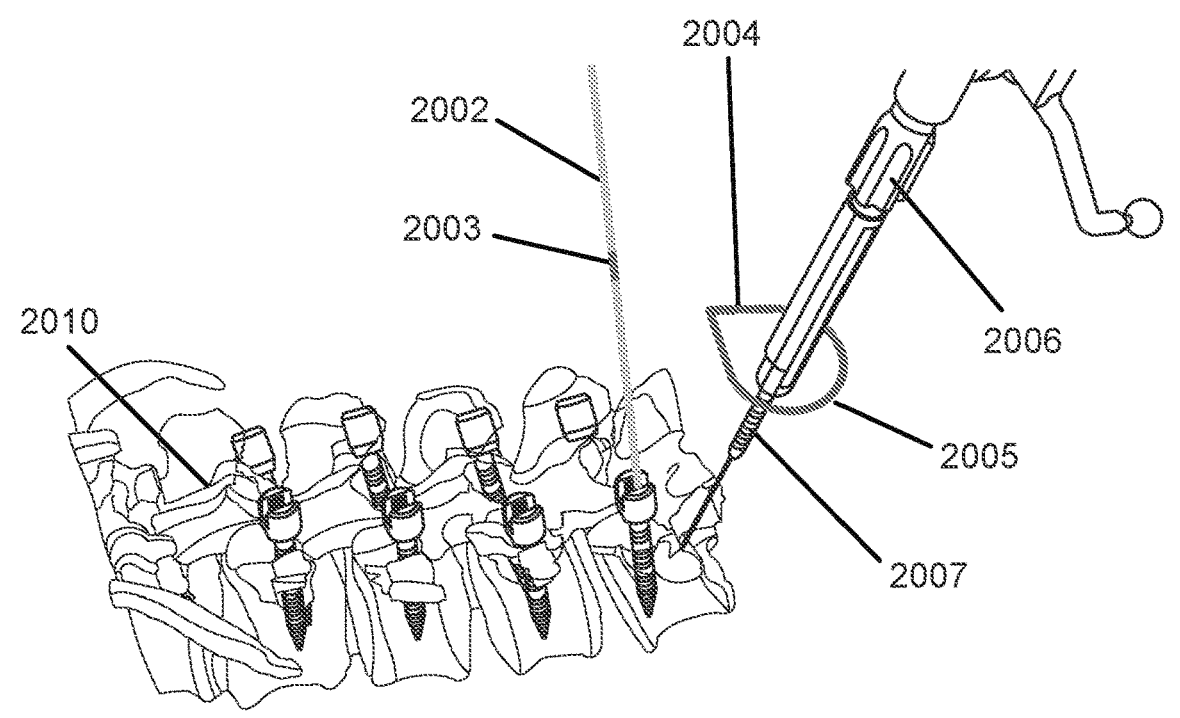
FIGS. 17A-17D are surgical navigation images, according to some embodiments.

FIG. 17A is a surgical navigation image based on patient anatomy data 2010 including a first virtual image 2002 corresponding to a planned position and/or orientation of a surgical instrument, and a second virtual image 2006 having an indicator 2005 corresponding to a current position and/or orientation of the surgical instrument (or a medical device (e.g., screw) coupled to the surgical instrument and depicted virtually as 2007). The first virtual image 2002 can include a section 2003 (e.g., indicator) that has different characteristics (e.g., thickness or color) that can indicate to a user where to intersect the indicator 2005 with the first virtual image 2002. As depicted in FIG. 17A, this section 2003 is shown in a first color (e.g., a darker color such as red), while the remaining sections of the first virtual image 2002 are shown in a second color (e.g., a lighter color such as green). The indicator 2005 can be a geometric shape (e.g., teardrop) located in a position corresponding to the current position and/or orientation of the surgical instrument. The indicator 2005 may include a set of peripheral markers 2004 (e.g., point of the teardrop) pointing toward the section 2003.

FIG. 17B is a surgical navigation image based on patient anatomy data 2110 including a first virtual image 2102 corresponding to a planned position and/or orientation of a surgical instrument, and a second virtual image 2106 having an indicator or directional marker 2105 corresponding to a current position and/or orientation of the surgical instrument (or a medical device (e.g., screw) coupled to the surgical instrument and depicted virtually as 2107). The first virtual image 2102 can include a section 2103 (e.g., indicator) that has different characteristics (e.g., thickness or color) that can indicate to a user where to intersect the indicator 2105 with the first virtual image 2102. As depicted in FIG. 17B, this section 2103 is shown in a first color (e.g., a darker color such as red), while the remaining sections of the first virtual image 2102 are shown in a second color (e.g., a lighter color such as green). The indicator 2105 can be a second geometric shape (e.g., arrow or triangle) located in a position corresponding to the current position and/or orientation of the surgical instrument.

Figure 17C:
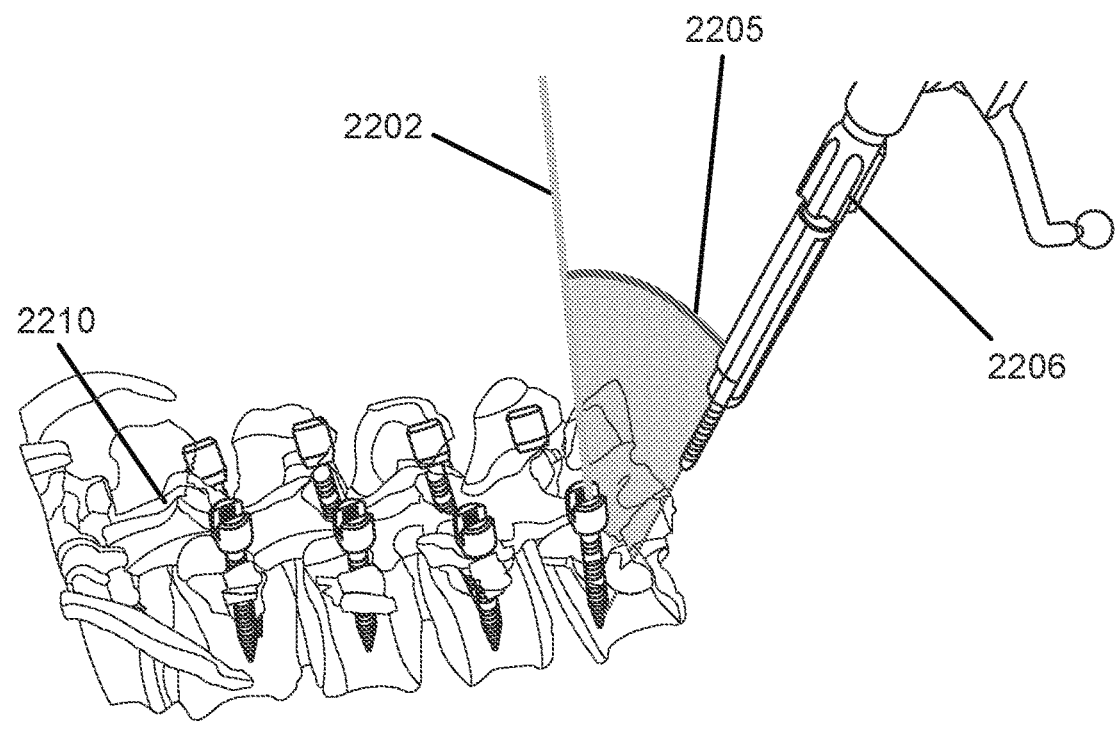

FIG. 17C is a surgical navigation image based on patient anatomy data 2210 including a first virtual image 2202 corresponding to a planned position and/or orientation of a surgical instrument, and a second virtual image 2206 corresponding to a current position and/or orientation of the surgical instrument. An indicator 2205 (e.g., pie shaped portion of a circle or other geometric shape) can be provided between the first and second virtual images 2202, 2206 to show an angle formed between the first virtual image 2202 and the second virtual image 2206. As the surgeon moves the surgical instrument toward the planned position and orientation, this indicator can get smaller, which can provide a guide to the surgeon that he is moving the surgical instrument in the right direction.

Figure 17D:
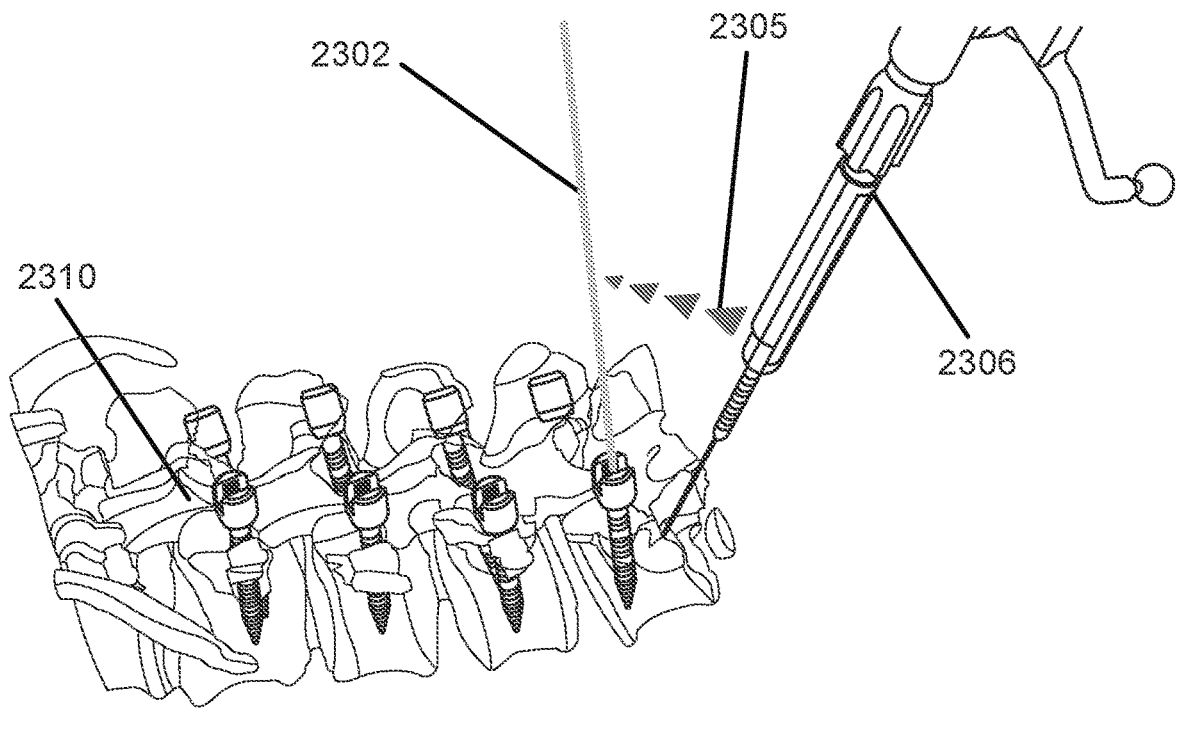

FIG. 17D is a surgical navigation image based on patient anatomy data 2310 including a first virtual image 2302 corresponding to a planned position and/or orientation of a surgical instrument 2307, and a second virtual image 2306 corresponding to a current position and/or orientation of the surgical instrument. An indicator 2305 (e.g., set of triangles or arrows) can be provided that points from the second virtual image 2306 toward the first virtual image 2202. The number of triangles may change based on the distance between the first virtual image 2302 and the second virtual image 2306, and as the surgeon moves the surgical instrument toward the first virtual image 2302, the number of triangles may decrease.

Figure 18:
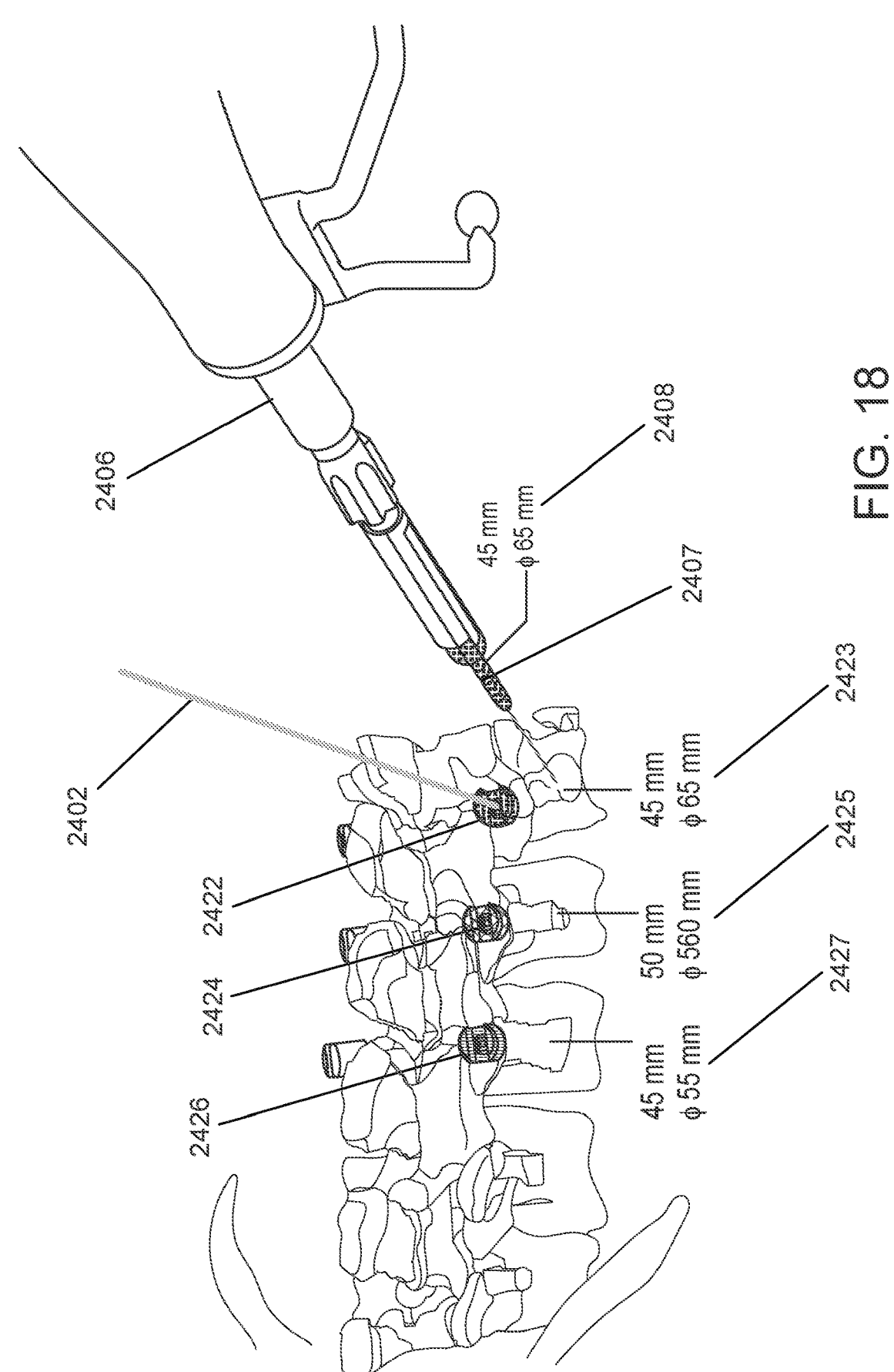
FIG. 18 is a surgical navigation image, according to some embodiments.

In some embodiments, multiple medical devices or implants (e.g. screw) may be planned for placement within a patient's anatomy. Each of these medical devices may have different characteristics, and it can be important to ensure that the medical devices are positioned at the right locations and not that corresponding to a different medical device. In such instances, different color coding (or different patterns, lines, or other characteristics) and/or information can be presented to assist a surgeon in identifying proper placement of a medical device. FIG. 18 is a surgical navigation image including a first medical device 2422, a second medical device 2424, a third medical device 2426, first virtual image 2402 corresponding to a planned position and/or orientation of a surgical instrument, and a second virtual image 2406 of the surgical instrument. In the real environment, the surgical instrument can be coupled to a medical device that is shown virtually as 2407. The first medical device 2422 can include a first indicator 2423 including a set of data corresponding to the first medical device 2422, the second medical device 2424 can include a second indicator 2425 including a set of data corresponding to the second medical device 2424, and the third medical device 2426 can include a third indicator 2427 including a set of data corresponding to the third medical device 2426. Based on the planned procedure, the medical device 2407 is to be placed at the location of the first medical device 2422. As such, based on the planned procedure, the surgeon is being guided to place the medical device 2407 at the location of the first medical device 2422. For example, the first virtual image 2402 can be a first geometric shape (e.g., line) located in a position corresponding to the planned position and/or orientation of the medical device 2407. Additionally or alternatively, the virtual representation of the medical device 2407 can be shown with the same color, pattern, etc. used to show the first medical device 2422, and a fourth indicator 2408 including a set of data corresponding to the medical device 2407 can be shown that is the same as that of the first indicator 2423. The second medical device 2424 and the third medical device 2426 (as well as their indicators) can be shown in different colors, patterns, etc. than the medical device 2407 (and its indicator).

Figures 19A, 19B:
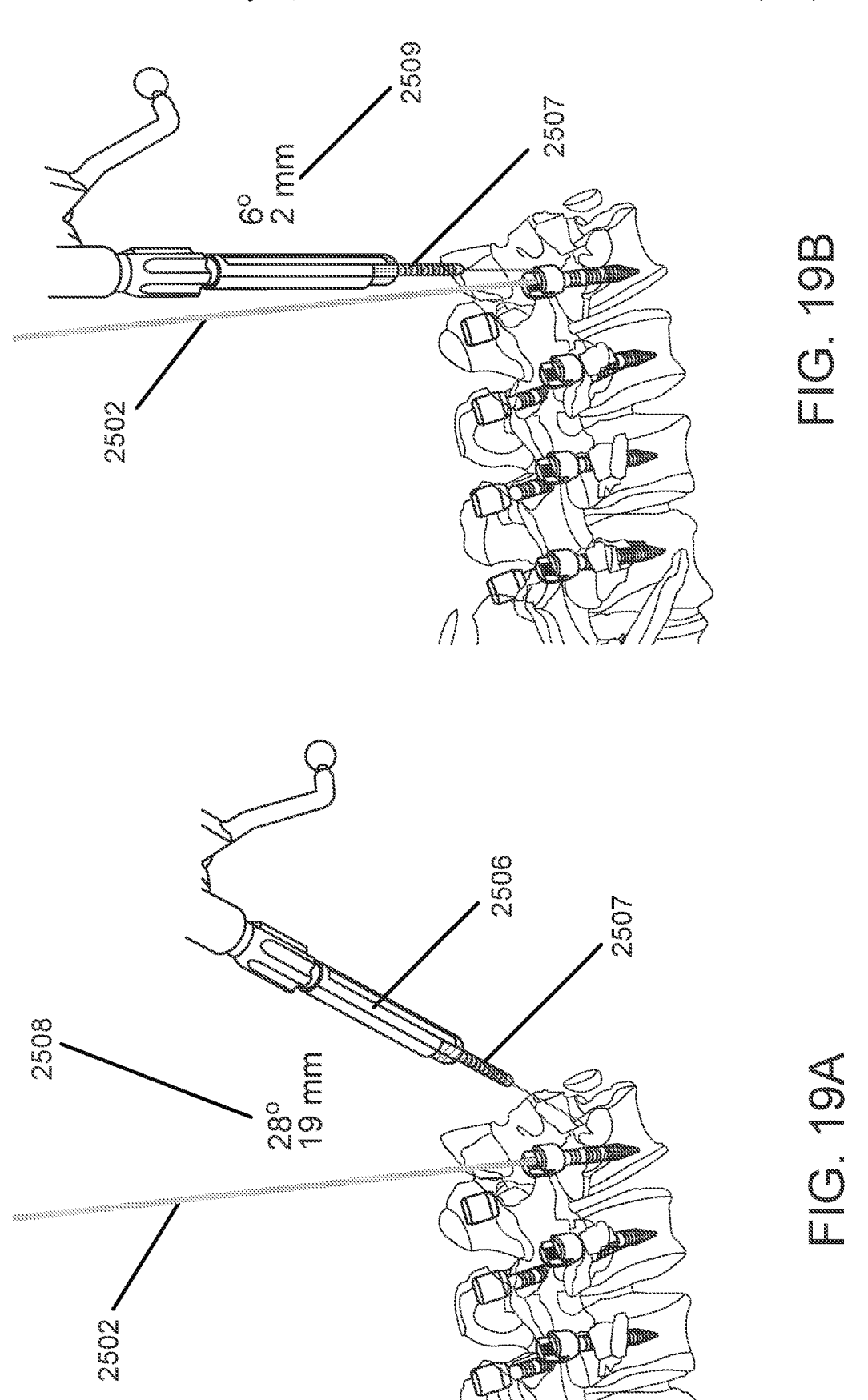
FIGS. 19A and 19B are surgical navigation images, according to some embodiments.

In some embodiments, different colors, patterns, or other characteristics can be used along with information associated with the current position and/or orientation of a medical device relative to its planned position and/or orientation to guide a surgeon. For example, FIGS. 19A and 19B are surgical navigation images including a first virtual element 2502 corresponding to a planned position and/or orientation of a surgical instrument, and a second virtual image 2506 corresponding to the current position and/or orientation of a surgical instrument. The surgical instrument can be coupled to a medical device (e.g., a screw) that is shown virtually as a screw 2507. In FIG. 19A, the screw 2507 and an indicator 2508 can be shown in a first color such as, for example, red, e.g., to indicate that the position and orientation of the surgical instrument and screw are outside of predetermined threshold values from the planned position and orientation. In FIG. 19B, the screw 2507 and an indicator 2509 can be shown in a second color such as, for example, green, e.g., to indicate that the position and orientation of the surgical instrument and screw are within the predetermined threshold values from the planned position and orientation. The change in the color can be used to indicate to the surgeon that the surgeon's manipulation of the surgical instrument is moving the surgical instrument toward its planned or planned position and orientation. The first and second indicators 2508, 2509 can also include information that informs the surgeon on how far off the surgeon is from the planned position and/or orientation of the screw. For example, indicator 2508 identifies that the screw is still 28 degrees off from the planned orientation of the screw and 19 millimeters (mm) away from the planned position of the screw, and indicator 2509 identifies that the screw is 6 degrees off from the planned orientation of the screw and 2 mm away from the planned position of the screw.

While two colors are described with reference to FIGS. 19A and 19B, it can be appreciated that additional colors can be used, e.g., to show when a medical device (e.g., screw) is within certain ranges from the planned orientation and/or position of the medical device. For example, a first color can be used to indicate when a screw is within a first range of distances from its planned position, a second color can be used to indicate when the screw is within a second range of distances from its planned position, and a third color can be used to indicate when the screw is within a third range of distances from its planned position.

3. Displaying a Virtual Representation of Patient Anatomy

FIG. 20 is a flow chart of a virtual representation display process 1700, according to embodiments. The process 1700 can be performed by one or more compute devices of a surgical navigation system, including, for example, compute device 210 or a processor of display system 240, wearable device 220, etc. At 1702, a virtual representation of patient anatomy may be displayed. For example, a set of anatomical structures of interest may be selectively displayed. Optionally, at 1704, a current position and/or orientation (P&O) of a medical device may be determined. At 1706, a virtual representation of a medical device may be displayed or updated based on a current position and/or orientation of the medical device. At 1707, one or more virtual elements associated with a position and/or orientation may be displayed or updated. Optionally, at 1708, one or more guidance cues indicating a direction of change between a current and planned position and/or orientation may be displayed or updated. Optionally, at 1710, a discrepancy between a current and planned position and/or orientation may be displayed or updated. At 1712, a determination may be made of whether the discrepancy is within a set of predefined criteria. If not, then the process may return to 1704 or 1706. If the discrepancy is within the predefined criteria, then the process 1700 may optionally proceed to one or more of 1714, 1716, and 1718. Optionally, at 1714, one or more indicators associated with a current position and/or orientation of the medical device may be displayed or updated. Optionally, at 1716, one or more indicators associated with a planned position and/or orientation of the medical device may be displayed or updated. Optionally, at 1718, a transient change may be applied to one or more virtual representations and/or virtual elements. The process may return to 1704 or 1706.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which examples have been provided. The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within +10% of 100 (e.g., from 90 to 110). The terms "about" and "approximately" may be used interchangeably.

Some embodiments and/or methods described herein can be performed by a different software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Python, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The invention claimed is:

1. An apparatus, comprising:
   a memory; and
   a processor operatively coupled to the memory, the processor configured to:
   determine, based on data associated with an operative plan of a surgical procedure, a planned position and orientation of a medical device in a patient anatomy, the medical device configured to be used in the surgical procedure;
   determine, based on tracking data associated with the medical device, a current position and orientation of the medical device;
   generate a three-dimensional (3D) image including:
   a first virtual image including a first indicator comprising a first geometric shape located within the 3D image at the planned position and a planned orientation of the medical device; and a second virtual image including a second indicator comprising a second geometric shape located within the 3D image at the current position and current orientation of the medical device;

modify the 3D image to change a location of the second indicator to reflect changes in the current position and orientation of the medical device;

determine that the current position and orientation of the medical device is near the planned position and orientation of the medical device based on at least one predefined criterion; and in response to determining that the current position and orientation of the medical device is near the planned position and orientation of the medical device;

modify at least one characteristic of the first virtual image or the second virtual image, wherein modifying the at least one characteristic includes modifying the second indicator to include a set of center markers located at or near a center of the first geometric shape when the first indicator and the second indicator overlap by a threshold amount.

2. The apparatus of claim 1, wherein the first geometric shape has a different shape than the second geometric shape.

3. The apparatus of claim 1, wherein:

the second geometric shape has at least one vertex, and in order to modify the 3D image, the processor is further configured to rotate the second geometric shape such that the at least one vertex moves to indicate a change in the current orientation of the medical device in response to the change in the current orientation of the medical device.

4. The apparatus of claim 1, wherein the first geometric shape has a color that is different from the second geometric shape.

5. The apparatus of claim 1, wherein in order to modify the at least one characteristic of the first virtual image or the second virtual image, the processor is further configured to modify a color of the second geometric shape.

6. The apparatus of claim 1, wherein in order to modify the at least one characteristic of the first virtual image or the second virtual image, the processor is further configured to modify the first virtual image to further include a set of peripheral markers located at or near the first geometric shape.

7. The apparatus of claim 6, wherein the set of peripheral markers include a set of geometric shapes or lines.

8. The apparatus of claim 6, wherein the processor is further configured to modify the at least one characteristic of a subset of the set of peripheral markers based on a deviation between the current position and orientation of the medical device and the planned position and orientation of the medical device.

9. The apparatus of claim 6, wherein in order to determine that the current position and orientation of the medical device is near the planned position and orientation of the medical device, the processor is further configured to determine that an overlap between the first geometric shape and the second geometric shape is greater than a threshold value.

10. The apparatus of claim 1, wherein the processor is configured to modify the at least one characteristic of the first virtual image or the second virtual image by changing a set of markers in the first virtual image.

11. The apparatus of claim 10, wherein in order to change the set of markers in the first virtual image, the processor is further configured to move the set of markers from being within the first geometric shape to being at or outside of a periphery of the first geometric shape.

12. The apparatus of claim 1, wherein in order to determine that the current position and orientation of the medical device is near the planned position and orientation of the medical device, the processor is further configured to determine that the second geometric shape has intersected the first geometric shape.

13. The apparatus of claim 1, wherein in order to determine that the current position and orientation of the medical device is near the planned position and orientation of the medical device, the processor is further configured to determine at least one of the current position of the medical device being less than a predefined distance from the planned position of the medical device or the current orientation of the medical device being less than a predefined angle from the planned position of the medical device.

14. The apparatus of claim 1, wherein the 3D image further includes a virtual representation of a portion of the patient anatomy.

15. The apparatus of claim 14, further comprising a display system configured to display the 3D image on a surface near a surgical field including the patient anatomy such that the virtual representation of the portion of the patient anatomy is displayed near the patient anatomy and the second virtual image is displayed near a portion of the medical device in a field of view of an operator.

16. The apparatus of claim 15, wherein the processor is further configured to:

determine, based on tracking data associated with a head of the operator, a position and orientation of the head of the operator; and generate the 3D image according to a perspective of the operator based on the position and orientation of the head of the operator.

17. The apparatus of claim 14, further comprising a display system configured to display the 3D image including the virtual representation of the portion of the patient anatomy and the first virtual image and the second virtual images in a field of view of an operator looking at a screen located near, inside, or outside of a surgical field.

18. The apparatus of claim 1, wherein the medical device includes a surgical instrument or an implant.

19. The apparatus of claim 1, wherein the first virtual image further includes a first set of peripheral markers located at or near the first geometric shape, and the second virtual image further includes a second set of peripheral markers located at or near the second geometric shape.

20. The apparatus of claim 19, wherein in order to modify the at least one characteristic of the first virtual image or the second virtual image, the processor is further configured to modify the second virtual image to remove the second set of peripheral markers located at or near the second geometric shape when the second indicator is enclosed by the first indicator.

21. A non-transitory processor-readable medium storing code that, when executed by a processor, cause the processor to:

determine, based on data associated with an operative plan of a surgical procedure, a planned position and orientation of a medical device in a patient anatomy, the medical device configured to be used in the surgical procedure;

determine, based on tracking data associated with the medical device, current position and orientation of the medical device;

generate a three-dimensional (3D) image including:
    a first virtual image including a first indicator compris-
        ing a first geometric shape located within the 3D
        image at the planned position and orientation of the
        medical device; and
    a second virtual image including a second indicator
        comprising a second geometric shape located within
        the 3D image at the current position and orientation
        of the medical device;
modify the 3D image to change a location of the second
    indicator to reflect changes in the current position and
    orientation of the medical device;
determine that the current position and orientation of the
    medical device is near the planned position and orien-
    tation of the medical device based on at least one
    predefined criterion; and
in response to determining that the current position and
    orientation of the medical device is near the planned
    position and orientation of the medical device:
    modify at least one characteristic of the first virtual
        image or the second virtual image,
    wherein in order to modify the at least one character-
        istic, the non-transitory processor-readable medium includes further code to cause the processor to
modify the second indicator to include a set of center
markers located at or near a center of the first
geometric shape when the first indicator and the
second indicator overlap by a threshold amount.

22. The non-transitory processor-readable medium of
claim 21, wherein:
    the first virtual image further includes a first set of
        peripheral markers located at or near the first geometric
        shape, and
    the second virtual image further includes a second set of
        peripheral markers located at or near the second geo-
        metric shape.

23. The non-transitory processor-readable medium of
claim 22, wherein in order to modify the at least one
characteristic of the first virtual image or the second virtual
image, the non-transitory processor-readable medium
includes further code to cause the processor to modify the
second virtual image to remove the second set of peripheral
markers located at or near the second geometric shape when
the second indicator is enclosed by the first indicator.

* * * * *